(12) United States Patent
Mould

(10) Patent No.: US 11,501,863 B2
(45) Date of Patent: Nov. 15, 2022

(54) SYSTEMS AND METHODS FOR PATIENT-SPECIFIC DOSING

(71) Applicant: Baysient LLC, Fort Myers, FL (US)

(72) Inventor: Diane R. Mould, Fort Myers, FL (US)

(73) Assignee: Diane R. Mould, Fort Myers, FL (US)

( * ) Notice: Subject to any disclaimer, the term of this patent is extended or adjusted under 35 U.S.C. 154(b) by 1565 days.

(21) Appl. No.: 15/094,379

(22) Filed: Apr. 8, 2016

(65) Prior Publication Data

US 2016/0300037 A1 Oct. 13, 2016

Related U.S. Application Data

(60) Provisional application No. 62/145,138, filed on Apr. 9, 2015.

(51) Int. Cl.
*G16H 20/10* (2018.01)
*G16H 20/17* (2018.01)

(52) U.S. Cl.
CPC ............ *G16H 20/10* (2018.01); *G16H 20/17* (2018.01)

(58) Field of Classification Search
CPC ....... G06Q 50/22–24; G16H 10/00–65; G16H 20/10; G16H 20/17; G06F 19/00; G06F 19/3456
USPC ........................................................ 705/2–3
See application file for complete search history.

(56) References Cited

U.S. PATENT DOCUMENTS

| | | |
|---|---|---|
| 5,365,948 A | 11/1994 | McMichael |
| 5,542,436 A | 8/1996 | McMichael |
| 5,694,950 A | 12/1997 | McMichael |
| 6,267,116 B1 | 7/2001 | McMichael |

(Continued)

FOREIGN PATENT DOCUMENTS

| | | |
|---|---|---|
| EP | 1725278 B1 | 8/2018 |
| WO | WO 2011059824 | 5/2011 |

(Continued)

OTHER PUBLICATIONS

Anderson, et al., "Clinical Pharmacokinetics Computer Programs," in: Pharmacy Informatics, Bourne, CRC Press (2010), pp. 199-216.

(Continued)

*Primary Examiner* — Michael Tomaszewski
(74) *Attorney, Agent, or Firm* — McDermott Will & Emery

(57) ABSTRACT

This disclosure relates to determining a personalized dose of a pharmaceutical for an individual. First data representative of one or more characteristics of the individual prior to administration of the pharmaceutical is received, and second data representative of a measurement of a physiological parameter of the individual after administration of the pharmaceutical is received. A computational model having pharmacokinetic and pharmacodynamic components is used to generate a first target concentration and one or more first doses determined to likely achieve the first target concentration for the pharmaceutical. The computational model is updated to reflect the measurement of the physiological parameter. A second target concentration and one or more second doses determined to likely achieve the second target concentration are generated, wherein the update to the pharmacodynamic component of the computational model is used to predict that the second target concentration will have a therapeutic effect on the individual.

20 Claims, 8 Drawing Sheets

(56) References Cited

U.S. PATENT DOCUMENTS

| | | | |
|---|---|---|---|
| 6,575,169 | B2 | 6/2003 | McMichael |
| 6,578,582 | B2 | 6/2003 | McMichael |
| 6,581,606 | B2 | 6/2003 | Kutzko et al. |
| 6,581,607 | B2 | 6/2003 | Kutzko et al. |
| 6,883,521 | B2 | 4/2005 | McMichael |
| 6,942,614 | B1 | 9/2005 | Kutzko et al. |
| 8,589,175 | B2 * | 11/2013 | Glauser .................. G06Q 50/24 705/2 |
| 10,083,400 | B2 | 9/2018 | Mould |
| 2003/0087848 | A1 | 5/2003 | Bratzler et al. |
| 2004/0122719 | A1 | 6/2004 | Sabol et al. |
| 2004/0122790 | A1 | 6/2004 | Walker et al. |
| 2005/0187789 | A1 | 8/2005 | Hatlestad et al. |
| 2005/0232927 | A1 | 10/2005 | Clarke et al. |
| 2006/0036619 | A1 | 2/2006 | Fuerst et al. |
| 2007/0099820 | A1 | 5/2007 | Lancaster et al. |
| 2007/0099926 | A1 | 5/2007 | Rodger et al. |
| 2008/0008991 | A1 * | 1/2008 | Groen .................... G01N 33/48 435/5 |
| 2008/0124689 | A1 | 5/2008 | Wiliams et al. |
| 2008/0188763 | A1 | 8/2008 | John et al. |
| 2008/0301077 | A1 | 12/2008 | Fung et al. |
| 2009/0006061 | A1 | 1/2009 | Thukral et al. |
| 2010/0273738 | A1 | 10/2010 | Vaicke et al. |
| 2011/0184267 | A1 | 7/2011 | Duke et al. |
| 2011/0229471 | A1 | 9/2011 | Rotter et al. |
| 2011/0306845 | A1 | 12/2011 | Osorio |
| 2011/0306846 | A1 | 12/2011 | Osorio |
| 2014/0114676 | A1 * | 4/2014 | Holmes .................. G01N 33/94 705/2 |
| 2014/0275164 | A1 | 9/2014 | Robinson et al. |
| 2014/0379629 | A1 | 12/2014 | Loew-Baselli et al. |

FOREIGN PATENT DOCUMENTS

| | | | |
|---|---|---|---|
| WO | WO-2014/055978 | A1 | 4/2014 |
| WO | WO-2014066428 | A1 | 5/2014 |
| WO | WO 2014173558 | | 10/2014 |

OTHER PUBLICATIONS

Anonymous: "Bayesian inference," Wikipedia, Oct. 2, 2012 (Oct. 2, 2012), XP055380922, Retrieved from the Internet: URL:https://en.wikipedia.otg/w/index.php?title=Bayesian_inferenced&oldid=515620785 [retrieved on Jun. 13, 2017].

Blau et al. "A Bayesian Pharmacometric Approach for Personalized Medicine—A Proof of Concept Study With Simulated Data" IEEE 2009 p. 1969-1976.

Wallin, Johan: "Dose Adaptation Based on Pharmacometric; Models" Iin: "Dose Adaptation Based on Pharmacometric; Models", Jan. 1, 2009 (Jan. 1, 2009), Uppsala: Acta; Universitatis Upsaliensis, Uppsala, Sweden, XP055271184,; ISSN: 1651-6182, ISBN: 978-91-5-547488-1.

Ahnstrom, et al., "A 6-year follow-up of dosing, coagulation factor levels and bleedings in relation to joint status in the prophylactic treatment of haemophilia," Haemophilia, 10, pp. 689-697 (2004).

Bjorkman, et al., "Population pharmacokinetics of recombinant factor VIII: the relationships of pharmacokinetics to age and body weight," Blood, 119, pp. 612-618 (2012).

Bjorkman, S. "Limited Blood Sampling for Pharmacokinetic Dose Tailoring of FVIII in the Prophylactic Treatment of Haemophilia A," Haemophilia, 16, pp. 597-605 (2010).

Bjorkman, S. "Prophylactic Dosing of Factor VIII and Factor XI from a Clinical Pharmacokinetic Perspective," Haemophilia, 9, pp. 101-110 (2003).

Carlsson, et al., "Pharmacokinetic Dosing in Prophylactic Treatment of Hemophilia A," European Journal of Haematology, 51, pp. 247-252 (1993).

Collins, et al., "Factor VIII requirement to maintain a target plasma level in the prophylactic treatment of severe hemophilia A: influences of variance in pharmacokinetics and treatment regimens," Journal of Thrombosis and Haemostasis, 8, pp. 269-275 (2009).

Collins, et al., "Implications of coagulation Factor VIII and IX Pharmacokinetics in the Prophylactic Treatment of Haemophilia," Haemophilia, 17 pp. 2-10 (2011).

Jelliffe, et al., "Individualizing Drug Dosage Regimens: Roles of Population Pharmacokinetic and Dynamic Models, Bayesian Fitting, and Adaptive Control," Therapeutic Drug Monitoring, 15, pp. 380-393 (1993).

Ljung, Rolf, "Prophylactic Therapy in Haemophilia," Blood Reviews, 23, pp. 267-274 (2009).

"Anonymouse: ""Ensemble learning,"" Wikipedia, Aug. 23, 2012, Retrieved from the Internet: URL:https://en.wikipedia.org/w/index.php?title=Ensemble_learning&oldid=508782155".

Ama, Evaluation of medical information science in medical education, National Library of Medicine, pp. 518-519 (Jan. 23, 1986) (58 pages).

Angelier, Evaluation of a nenatal hyperalimentation microcomputer program, The University of Arizona, pp. 79, 84 (1988) (255 pages).

Assenmacher-Wesche and Pesaran, Forecasting the Swiss economy using VECX models: an exercise in forecast combination across modeals and obsrevation windows, National Institute Economic Review No. 203, 18 pages (Jan. 2008).

Fasanmade et al., "Population pharmacokinetic analysis of infliximab in patients with ulcerative colitis," Eur J Clin Pharmacol., 65:1211-1228 (2009).

Goel, Application of an active comparator-based benefit-risk assessment in evaluating clinical trial design features of a new chemical entity using a Bayesian decision-theorectic framework, a dissertation submitted to the faculty of the Graduate School of the University of Minnesota, pp. 17-36 (Jun. 2010) (142 pages).

http://doseme.com.au/index.html, retrived from the Internet on Nov. 5, 2014, pp. 1-3.

http://pkb.chop.edu/index.php, retrieved from the Internet on Nov. 5, 2014, pp. 1-3.

http://www.firstdose.org/, retrieved from the Internet on Nov. 5, 2014, 1 page.

http://www.lapk.org/RightDose_manual.pdf, retrieved from the Internet on Nov. 10, 2014, pp. 1-114.

http://www.mediware.cz/index_en.html, retrieved from the Internet on Nov. 5, 2014, pp. 1-2.

http://www.meds.com/DoseCalc/dcintro.html, retrieved from the Internet on Nov. 10, 2014, pp. 1-2.

http://www.rxkinetics.com/, retrieved from the Internet on Nov. 5, 2014, one page.

http://www.tciworks.info/, retrieved from the Internet on Nov. 5, 2014, pp. 1-3.

http://www.tdms2000.com/, retrieved from the Internet on Nov. 5, 2014, pp. 1-2.

http://www.testandcalc.com/drugcalc/index.asp, retrieved from Internet on Nov. 5, 2014, pp. 1-2.

http://www.warfarindosing.org/Source/Home.aspx, retrieved from the Internet on Nov. 5, 2014, one page.

International Preliminary Report on Patentability and Written Opinion in International Application No. PCT/US2013/063691 dated Apr. 16, 2015.

International Search Report and Written Opinion for International Application No. PCT/US2016/026562 dated Jul. 18, 2016.

International Search Report for International Application No. PCT/US2013/063691 dated Mar. 5, 2014.

Montazeri, Ashraf, et al., "Individual Adaptive Dosing of Topotecan in Ovarian Cancer," Clin Cancer Res Feb. 2002;8:394-399 (downloaded from clincancerres.aacrjournals.org on Jul. 7, 2012).

Mould et al., "Basic concepts in population modeling, simulations, and model-based drug development," Pharmacometrics & Systems Pharamacology, 1, e6 (2012) (14 pages).

Mould, et al "Dashboard Systems: Pharmacokinetic/Pharmacodynamic Mediated Dose Optimization for Monoclonal Antibodies," The Journal of Clinical Pharmacology, 55:S3, published online Feb. 23, 2015, pp. S51-S59.

Mould, et al, "Dashboard Systems: Implementing Pharmacometrics from Bench to Bedside," The AAPS Journal, 16:5, Sep. 2014, pp. 925-937.

(56) References Cited

OTHER PUBLICATIONS

Tobler, Andrea et al., "Intravenous phenytoin: a retrospective analysis of Bayesian forecasting versus conventional dosing in patients," Int J Clin Pharm (Jun. 29, 2013) 35:790-797.

Yin et al., "Bayesian model averaging continual reassessment method in Phase 1 clinical trials," Journal of the American Statistical Association, 104:954-968.

Barrett, et al, "Integration of Modeling and Simulation into Hospital-based Decision Support Systems Guiding Pediatric Pharmacotherapy," BMC Medical Informatics and Decision Making Biomed Central, London, GB, vol. 8, No. 1, p. 6, Jan. 28, 2008.

Fasanmade et al., "Pharmacokinetic Properties of Infliximab in Children and Adults with Crohn's Disease: A Retrospective Analysis of Data from 2 Phase III Clinical Trials", Clinical Therapeutics, Excerpta Medica, Princeton, NJ, vol. 33, No. 7, pp. 946-964, Jun. 1, 2011.

Furuya, et al, "Theory Based Analysis of Anti-Inflammatory Effect of Infliximab on Crohn's Disease," Drug Metab. Pharmacokinet, pp. 20-25, Aug. 25, 2006.

Kimura, et al, "Theory-Based analysis of Anti-Inflammatory Effect of Infliximab on Crohn's Disease and Rheumatoid Arthritis" Rheumatology International; Clinical and Experimental Investigations, Springer Berlin, DE, vol. 32, No. 1, pp. 145-150, Aug. 1, 2010.

Mould et al., "Basic concepts in population modeling, simulations, and model-based drug development—Part 2: Introduction to Pharmacokinetic Modeling Methods", CPT: Pharmacometrics & Systems Pharmacology, vol. 2, No. 4, p. e38, Apr. 1, 2013.

Upton, et al, "Basic Concepts in Population Modeling, Simulation, and Model-Based Drug Development: Part 3—Introduction to Pharmacodynamic Modeling Methods", CPT: Pharmacometrics & Systems Pharmacology, vol. 3, No. 1, p. e88, Jan. 2, 2014.

Xu, et al, "Population Pharmacokinetics of Infliximab in Patients with Ankylosing Spondylitis", Journal of Clinical Pharmacology, Vo. 48, No. 6, pp. 681-695 Jun. 1, 2008.

Chirmule, N. , et al., "Immunogenicity to Therapeutic Proteins: Impact on PK/PD and Efficacy", The AAPS Journal, Springer US, Boston, vol. 14, No. 2, 2012, pp. 296-302 (2012).

International Search Report for International Application No. PCT/US2019/028750 dated Aug. 16, 2019.

International Search Report for International Application No. PCT/US2020/021742 dated Jun. 19, 2020.

Yan, X. et al., "Population Pharmacokinetic and Pharmacodynamic Model-Based Comparability Assessment of a Recombinant Human Epoetin Alfa and the Biosimilar HX575", The Journal of Clinical Pharmacology, vol. 52, No. 11, Nov. 1, 2012 (Nov. 1, 2012), pp. 1624-1644 (2012).

Dubinsky M.C. et al., Pharmacokinetic Dashboard-Recommended Dosing Is Different than Standard of Care Dosing in Infliximab-Treated Pediatric IBD Patients. The AAPS Journal, Jul. 31, 2017, vol. 19, No. 1, pp. 215-222 (2017).

\* cited by examiner

| Home | myPatients ▼ | About | Log Out Logged in as Diane Mould | | | | | |
|------|------|------|------|------|------|------|------|------|
| | All Patients | Patient Details | Entries | New Entry | Medications | | | |
| | | | Patient 849808200 | | Forecast | | | |

When to Dose | Try a Dose | Find a Dose | History

Find the dose for the next trough concentration

Plot Table

Show [25 ▼] entries                                                Search: [        ]

| Dose Date ◆ | Dose Interval ◆ | Trough Date ◆ | Dose (mg) ◆ | Dose (mg/kg) ◆ | Dose (vials) ◆ | Target (ng/ml) ◆ |
|---|---|---|---|---|---|---|
| 2015-01-02 | 8 week | 2015-02-27 | | too high | | 3 |
| 2015-01-02 | 7 week | 2015-02-20 | | too high | | 3 |
| 2015-01-02 | 6 week | 2015-02-13 | | too high | | 3 |
| 2015-01-02 | 5 week | 2015-02-06 | 639.7 | 9.14 | 6.4 | 3 |
| 2015-01-02 | 4 week | 2015-01-30 | 490.4 | 7.01 | 4.9 | 3 |
| 2015-01-02 | 3 week | 2015-01-23 | 341.3 | 4.88 | 3.4 | 3 |
| 2015-01-02 | 2 week | 2015-01-16 | 169.6 | 2.42 | 1.7 | 3 |

[DoseDate] [DoseInterval] [TroughDate] [Dose(mg)] [Dose(mg/kg)] [Dose(vials)] [Target(ng/ml)]

Previous | 1 | Next

Dose interval mode
● Automatic
○ Manual

Plot options
[Concentration ▼]

[✕ Save Doses]

FIG. 5B

SYSTEMS AND METHODS FOR PATIENT-SPECIFIC DOSING

CROSS-REFERENCE TO RELATED APPLICATION

This application claims the benefit of priority to U.S. provisional application Ser. No. 62/145,138, filed Apr. 9, 2015, which is hereby incorporated by reference in its entirety.

TECHNICAL FIELD

This disclosure relates generally to patient-specific dosing and treatment recommendations including, without limitation, computerized systems and methods that use medication-specific mathematical models and observed patient-specific responses to treatment, to predict, propose, and evaluate suitable medication treatment plans for a specific patient.

BACKGROUND

A physician's decision to start a patient on a medication-based treatment regimen involves development of a dosing regimen for the medication to be prescribed. Different dosing regimens will be appropriate for different patients having differing patient factors. By way of example, dosing quantities, dosing intervals, treatment duration and other variables may be varied. Although a proper dosing regimen may be highly beneficial and therapeutic, an improper dosing regimen may be ineffective or deleterious to the patient's health. Further, both under-dosing and overdosing generally results in a loss of time, money and/or other resources, and increases the risk of undesirable outcomes.

In current clinical practice, the physician typically prescribes a dosing regimen based on dosing information contained in the package insert (PI) of the prescribed medication. In the United States, the contents of the PI are regulated by the Food and Drug Administration (FDA). As will be appreciated by those skilled in the art, the PI is typically a printed informational leaflet including a textual description of basic information that describes the drug's appearance, and the approved uses of the medicine. Further, the PI typically describes how the drug works in the body and how it is metabolized. The PI also typically includes statistical details based on trials regarding the percentage of people who have side effects of various types, interactions with other drugs, contraindications, special warnings, how to handle an overdose, and extra precautions. PIs also include dosing information. Such dosing information typically includes information about dosages for different conditions or for different populations, like pediatric and adult populations. Typical PIs provide dosing information as a function of certain limited patient factor information. Such dosing information is useful as a reference point for physicians in prescribing a dosage for a particular patient.

Dosing information is often developed by the medication's manufacturer, after conducting clinical trials involving administration of the drug to a population of test subjects, carefully monitoring the patients, and recording of clinical data associated with the clinical trial. The clinical trial data is subsequently compiled and analyzed to develop the dosing information for inclusion in the PI. The typical dosing information is a generic reduction or composite, from data gathered in clinical trials of a population including individuals having various patient factors, that is deemed to be suitable for an "average" patient having "average" factors and/or a "moderate" level of disease, without regard to many of any specific patient's factors, including some patient factors that may have been collected and tracked during the clinical trial. By way of example, based on clinical trial data gathered for Abatacept, an associated PI provides indicated dosing regimens with a very coarse level of detail—such as 3 weight ranges (<60 kg, 60-100 kg, and >100 kg) and associated indicated dosing regimens (500 mg, 750 mg, and 1000 mg, respectively). Such a coarse gradation linked to limited patient factors (e.g., weight), ignores many patient-specific factors that could impact the optimal or near optimal dosing regimen. Accordingly, it is well-understood that a dosing regimen recommended by a PI is not likely to be optimal or near-optimal for any particular patient, but rather provides a safe starting point for treatment, and it is left to the physician to refine the dosing regimen for a particular patient, largely through a trial and error process.

The physician then determines a dosing regimen for the patient as a function of the PI information. For example, the indicated dosing regimen may be determined to be 750 mg, every 4 weeks, for a patient having a weight falling into the 60-100 kg weight range. The physician then administers the indicated dosing regimen by prescribing the medication, causing the medication to be administered and/or administering a dose to the patient consistent with the dosing regimen.

As referenced above, the indicated dosing regimen may be a proper starting point for treating a hypothetical "average" patient, but the indicated dosing regimen is very likely not the optimal or near-optimal dosing regimen for the specific patient being treated. This may be due, for example, to the individual factors of the specific patient being treated (e.g., age, concomitant medications, other diseases, renal function, etc.) that are not captured by the factors accounted for by the PI (e.g., weight). Further, this may be due to the coarse stratification of the recommended dosing regimens (e.g., in 40 kg increments), although the proper dosing is more likely a continuously variable function of one or more patient factors.

Current clinical practice acknowledges this discrepancy. Accordingly, it is common clinical practice to follow-up with a patient after an initial dosing regimen period to reevaluate the patient and dosing regimen. Accordingly, the physician may next evaluate the patient's response to the indicated dosing regimen. By way of example, this may involve examining the patient, drawing blood or administering other tests to the patient and/or asking for patient feedback, such that the patient's response to the previously-administered dosing regimen may be observed by the treating physician. As a result of the evaluation and observed response, the physician determines whether a dose adjustment is warranted, e.g., because the patient response is deficient.

If a dose adjustment is not warranted, then the physician may discontinue dosing adjustments. If, however, a dose adjustment is warranted, then the physician will adjust the dosing regimen ad hoc. Sometimes the suitable adjustment is made solely in the physician's judgment. Often, the adjustment is made in accordance with a protocol set forth in the PI or by instructional practice. By way of example, the PI may provide quantitative indications for increasing or decreasing a dose, or increasing or decreasing a dosing interval. In either case, the adjustment is made largely on an ad hoc basis, as part of a trial and error process, and based largely on data gathered after observing the effect on the patient of the last-administered dosing regimen.

After administering the adjusted dosing regimen, the patient's response to the adjusted dosing regimen is evaluated. The physician then again determines whether to adjust the dosing regimen, and the process repeats. Such a trial-and-error based approach relying on generic indicated dosing regimens and patient-specific observed responses works reasonably well for medications with a fast onset of response. However, this approach is not optimal, and often not satisfactory, for drugs that take longer to manifest a desirable clinical response. Further, a protracted time to optimize dosing regimen puts the patient at risk for undesirable outcomes.

SUMMARY

Accordingly, systems and methods are disclosed herein for predicting, proposing and/or evaluating suitable medication dosing regimens for a specific individual as a function of individual-specific characteristics that eliminates or reduces the trial and error aspect of conventional dosing regimen development, and that shortens the length of time to develop a satisfactory or optimal dosing regimen, and thus eliminates or reduces associated waste of medications, time or other resources and reduces the risk of undesirable outcomes.

One aspect relates to a system for determining a personalized dose of a pharmaceutical for an individual. As discussed in detail below, the system may be a computer system including a single computer or multiple computers communicating over any network, such as in distributed architecture. At least one processor may be housed in one, some, or all of the computers in the computer system, and may be in communication with at least one electronic database stored on the same computer or on a different computer within the computer system. The system may include a cloud-based set of computing system operated by the same, related, or unrelated entities.

The system includes an input port configured to receive first data representative of one or more characteristics of the individual prior to administration of the pharmaceutical and second data representative of a measurement of a physiological parameter of the individual after administration of the pharmaceutical. A computer processor is in communication with the input port and an electronic database having information that represents a computational model to predict an effect of the pharmaceutical on the individual's body. The computational model including a pharmacokinetic component and a pharmacodynamic (e.g., response to treatment) component, and the computer processor is configured to generate, based on the first data and the computational model, a first target concentration and one or more first doses determined to likely achieve the first target concentration for the pharmaceutical in the individual's body. In particular, the one or more first doses may be included in one or more dose regimens, where each dose regimen includes an amount (or dosage) of the pharmaceutical to administer to the individual, as well as a frequency or time interval between doses. In general, a dose regimen may include a single dose, multiple doses with the same amounts, or multiple doses with different amounts. Moreover, a dose regimen may include fixed time intervals or varying time intervals between doses. Then, the computer processor computes, based on the second data, an update to the pharmacokinetic component and the pharmacodynamic component of the computational model to obtain an updated computational model that reflects the measurement of the physiological parameter. Based on the updated computational model, a second target concentration and one or more second doses determined to likely achieve the second target concentration for the pharmaceutical in the individual's body are generated. The update to the pharmacodynamic component of the computational model is used to predict that the second target concentration will have a therapeutic effect on the individual. To comply with HIPAA requirements, the first data and the second data may each include an anonymized identifier for the individual.

In some implementations, the pharmacokinetic component of the computational model includes a compartmental model, and the computer processor is configured to use the pharmacokinetic component to predict a concentration time profile of the pharmaceutical in at least one compartment in the compartmental model. The predicted concentration time profile is predicted by using a first differential equation that describes a flow rate of the pharmaceutical into and out of the at least one compartment in the compartmental model. The pharmacodynamic component of the computational model may include a differential equation that includes a synthesis rate parameter representative of a synthesis rate of a pharmacodynamic marker and a degradation rate parameter representative of a degradation rate of the pharmacodynamic marker and a drug effect component that is reflective of the expected response to therapy of the chosen therapeutic agent. The synthesis rate parameter, the degradation rate parameter, and the drug effect parameters are used in a second differential equation that predicts the individual's response to the pharmaceutical.

In some implementations, the physiological parameter is a measured concentration time profile of the pharmaceutical in the individual's blood, tissue, or cells, and the computer processor generates the second target concentration and the one or more doses by comparing the measured concentration time profile to the predicted concentration time profile. The computational model is then updated to modify the predicted concentration time profile such that it better matches the measured concentration time profile. In particular, this update may include updating the pharmacodynamics component of the computational model to assess the patient's individual responsiveness to the therapy and to achieve a particular target concentration. The computer processor generates the second target concentration and the one or more second doses by performing an optimization technique to minimize a difference between the measured concentration time profile and the predicted concentration. In an illustrative example, the pharmaceutical is infliximab, and the pharmacodynamic component of the computational model reflects an effect of infliximab on the individual's body, which is reflected by an altered formation or degradation flow rate based on the drug effect parameters. The modified flow rate accounts for the individual's predicted response to the infliximab as the individual heals from his or her disease state. The first target concentration and the second target concentration may each correspond to a concentration that is predicted to cause and maintain an effect in the individual's body.

In some implementations, the first target concentration and the one or more first doses are portions of a first dosing regimen that includes recommended times and doses to administer to the individual. In this case, the input port may be further configured to receive third data indicative of one or more requirements set by a manufacturer of the pharmaceutical, and the computer processor is further configured to modify the first dosing regimen to comply with the one or more requirements while simultaneously using the computational model to reduce an adverse effect of modifying the first dosing regimen.

Another aspect relates to a non-transitory computer readable medium storing computer-executable instructions that, when executed by at least one computer processor, cause a computer system to perform a method for determining a personalized dose of a pharmaceutical for an individual. The method includes receiving, at an input port, first data representative of one or more characteristics of the individual prior to administration of the pharmaceutical. The method also includes generating, at a computer processor, based on the first data and a computational model, a first target concentration and one or more first doses determined to likely achieve the first target concentration for the pharmaceutical in the individual's body, wherein the computer processor is in communication with the input port and an electronic database having information that represents the computational model to predict an effect of the pharmaceutical on the individual's body, the computational model including a pharmacokinetic component and a pharmacodynamic component. Second data is received at the input port, where the second data is representative of a measurement of a physiological parameter of the individual after administration of the pharmaceutical. The method includes computing, based on the second data, an update to the pharmacokinetic component and the pharmacodynamic component of the computational model to obtain an updated computational model that reflects the measurement of the physiological parameter. Then, based on the updated computational model, a second target concentration and one or more second doses determined to likely achieve the second target concentration and achieve a desired response for the pharmaceutical in the individual's body are generated, wherein the update to the pharmacodynamic component of the computational model is used to predict that the second target concentration will have a therapeutic effect on the individual.

BRIEF DESCRIPTION OF THE DRAWINGS

The above and other features of the present disclosure, including its nature and its various advantages, will be more apparent upon consideration of the following detailed description, taken in conjunction with the accompanying drawings in which:

FIGS. 5A and 5B are example displays of a user interface on a clinical portal that provide several recommended dosing regimens, according to an illustrative implementation.

DETAILED DESCRIPTION

Figure 1:
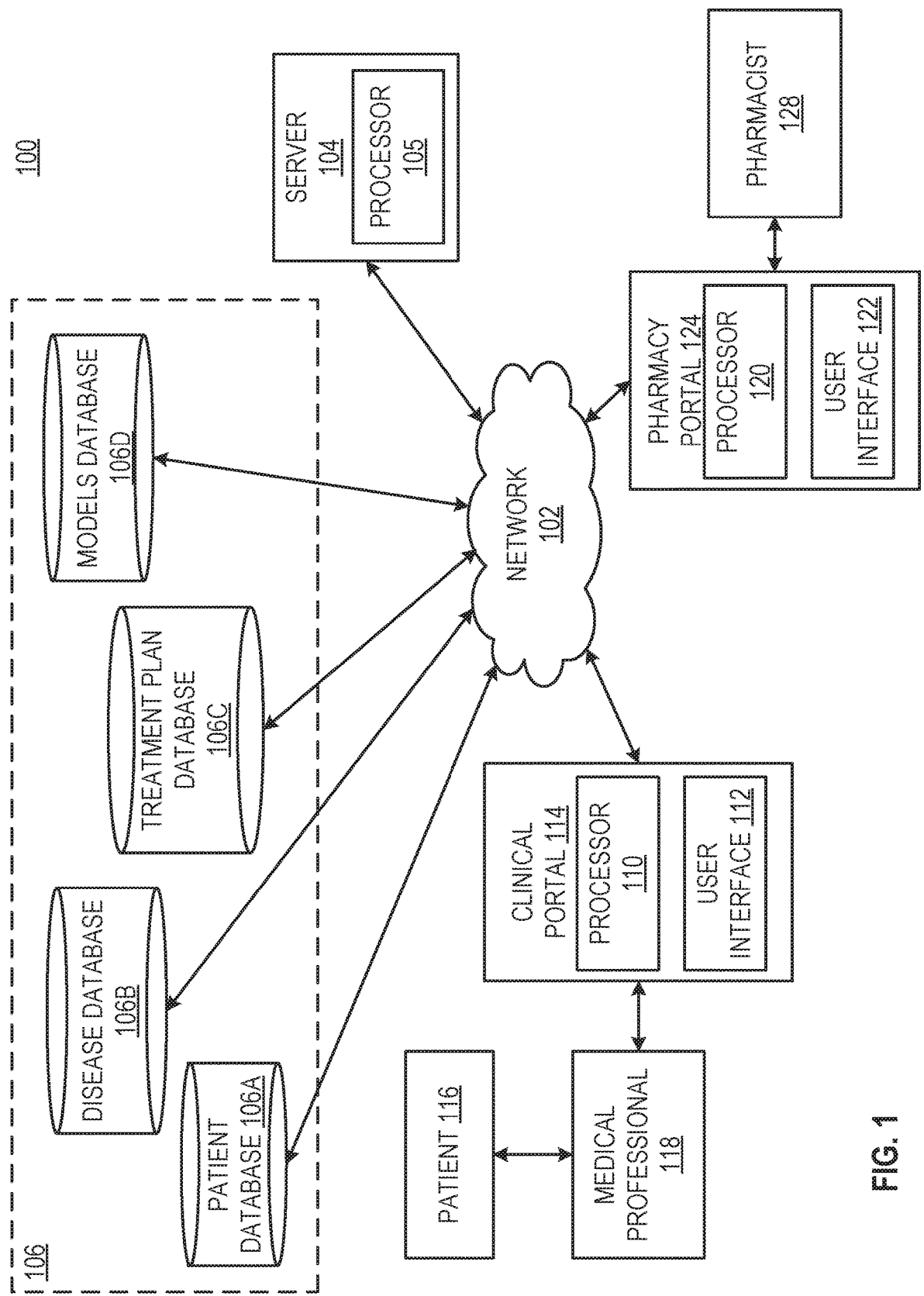
FIG. 1 is a block diagram of a computerized system for using medication-specific mathematical models and observed patient-specific responses to treatment to predict, propose, and evaluate suitable medication treatment plans for a specific patient, according to an illustrative implementation.

Described herein are medical treatment analysis and recommendation systems and methods that provide a tailored approach to analyzing patient measurements and to generating recommendations that are responsive to a patient's specific response to a treatment plan. To provide an overall understanding, certain illustrative implementations will now be described, including a system for predicting a patient's response to a treatment plan and providing a patient-specific dosing regimen. However, it will be understood by one of ordinary skill in the art that the systems and methods described herein may be adapted and modified as is appropriate for the application being addressed and may be employed in other suitable applications, and that such other additions and modifications will not depart from the scope thereof.

The present disclosure provides systems and methods for providing patient-specific medication dosing as a function of mathematical models updated to account for an observed patient response, such as a blood concentration level, or a measurement such as blood pressure or hematocrit. In particular, the systems and methods described herein involve predicting, proposing and/or evaluating suitable medication dosing regimens for a specific individual as a function of individual-specific characteristics and observed responses of the specific individual to the medication. Conceptually, the prescribing physician is provided with access, in a direct way, to mathematical models of observed patient responses to a medication when prescribing the medication to a specific patient. In prescribing a treatment plan for a patient, the mathematical model is used to predict a specific patient's response as a function of patient-specific characteristics that are accounted for in the model as patient factor covariates. Accordingly, the prescribing physician is able to leverage the model in developing a reasonably tailored treatment plan for a specific patient, as a function of the specific patient's characteristics, with much greater precision than a PI can provide.

Bayesian analysis may be used to determine a recommended dosing regimen. This is described in detail in U.S. patent application Ser. No. 14/047,545, filed Oct. 7, 2013 and entitled "System and method for providing patient-specific dosing as a function of mathematical models updated to account for an observed patient response" ("the '545 application"), which is incorporated herein by reference in its entirety. As is described in the '545 application, a Bayesian analysis may be used to determine an appropriate dose needed to achieve a desirable result, such as maintaining a drug's concentration in the patient's blood near a particular level. In particular, the Bayesian analysis may involve Bayesian averaging, Bayesian forecasting, and Bayesian updating.

Importantly, not only do the systems and methods of the present disclosure provide a recommendation for a dosing regimen to achieve a particular target level for a physiological parameter in a specific patient (such as the concentration level of a drug or biomarker in the patient's blood, for example), but the present disclosure also provides a way to determine whether that particular target level would be effective for the specific patient. In one example, as is shown and described in relation to FIG. 2, the mathematical model includes a pharmacokinetic (PK) model (that predicts the time course of the presence of a drug in a body) and a pharmacodynamic (PD) model (that predicts the resulting therapeutic and/or adverse effects of a drug in a body) combined together. As is explained in relation to FIG. 2, the resulting pharmacokinetic/pharmacodynamic (PK/PD) model provides a recommendation for a specific target level that is predicted to result in a therapeutic response for a particular patient.

In addition, the specific patient's observed response to the initial dosing regimen is used to adjust the dosing regimen. Specifically, the patient's observed response is used in conjunction with the mathematical model and patient-specific characteristics to account for between-subject-variability (BSV) that cannot be accounted for by the mathematical model alone. Accordingly, the observed responses of the specific patient can be used to refine the models and related forecasts, to effectively personalize the models so that they may be used to forecast expected responses to proposed dosing regimens more accurately for a specific patient. In this manner, observed patient-specific response data is effectively used as "feedback" to adapt a generic model describing typical patient response to a patient-specific model capable of accurately forecasting a patient-specific response, such that a patient-specific dosing regimen can be predicted, proposed and/or evaluated on a patient-specific basis. Using the observed response data to personalize the models allows the models to be modified to account for BSV that is not accounted for in previous mathematical models, which described only typical responses for a patient population, or a "typical for covariates" response for a typical patient having certain characteristics accounted for as covariates in the model.

The systems and methods of the present disclosure allows the prescribing physician to develop a personalized dosing regimen using one or more mathematical models reflecting actual clinical data, without the loss of resolution in the data and/or model that results from distillation of the actual clinical data into a relatively coarsely stratified set of recommendations for an "average" or "typical" patient, as in a PI. The model-based development of such patient-specific medication dosing regimens eliminates or reduces the trial-and-error aspect of conventional dosing regimen development. Further, such model-based development shortens the length of time to develop a satisfactory or optimal dosing regimen, and thus eliminates or reduces associated waste of medications, time or other resources, as well as reduces the amount of time that a patient is at risk of undesirable outcomes.

Generally, mathematical models developed from clinical data are gathered from patients to whom a particular medication had been administered. These models are processed to create a composite model rich in patient data, and patient-specific dosing regimens are determined as a function of patient-specific observed response data processed in conjunction with data from the mathematical models. More specifically, as is described in the '545 application, Bayesian averaging, Bayesian updating, and Bayesian forecasting techniques may be used to develop patient-specific dosing regimens as a function of not only generic mathematical models and patient-specific characteristics accounted for in the models as covariate patient factors, but also observed patient-specific responses that are not accounted for within the models themselves, and that reflect BSV that distinguishes the specific patient from the typical patient reflected by the model.

In this manner, the present disclosure accounts for variability between individual patients that is unexplained and/ or unaccounted for by traditional mathematical models (e.g., patient response that would not have been predicted based solely on the dose regimen and patient factors). Further, the present disclosure allows patient factors accounted for by the models, such as weight, age, race, laboratory test results, etc., to be treated as continuous functions rather than as categorical (cut off) values. By doing this, known models are adapted to a specific patient, such that patient-specific forecasting and analysis can be performed, to predict, propose and/or evaluate dosing regimens that are personalized for a specific patient. Notably, the present disclosure may be used to not only retroactively assess a dosing regimen previously administered to the patient, but also to prospectively assess a proposed dosing regimen before administering the proposed dosing regimen to the patient, or to identify dosing regimens (administered dose, dose interval, and route of administration) for the patient that will achieve the desired outcome.

By refining a particular patient's initial dosing regimen as a function of observed patient-specific data, in view of the composite mathematical model, a personalized, patient-specific dosing regimen is developed, and further is developed quickly. It will be appreciated that the exemplary method is implemented and carried out by a computerized model-based patient specific medication dosing regimen recommendation system 100 with input provided by a human operator, such as a physician or other medical professional, and thus acts as a recommendation engine and/or physician's expert system providing information for consideration by a prescribing physician.

FIG. 1 is a block diagram of a computerized system 100 for implementing the systems and methods disclosed herein. In particular, the system 100 uses medication-specific mathematical models and observed patient-specific responses to treatment to predict, propose, and evaluate suitable medication treatment plans for a specific patient. The system 100 includes a server 104, a clinical portal 114, a pharmacy portal 124, and an electronic database 106, all connected over a network 102. The server 104 includes a processor 105, the clinical portal 114 includes a processor 110 and a user interface 112, and the pharmacy portal 124 includes a processor 120 and a user interface 122. As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data that is currently being processed. An illustrative computing device 600, which may be used to implement any of the processors and servers described herein, is described in detail below with reference to FIG. 6. As used herein, "user interface" includes, without limitation, any suitable combination of one or more input devices (e.g., keypads, touch screens, trackballs, voice recognition systems, etc.) and/or one or more output devices (e.g., visual displays, speakers, tactile displays, printing devices, etc.). As used herein, "portal" includes, without limitation, any suitable combination of one or more devices configured with hardware, firmware, and software to carry out one or more of the computerized techniques described herein. Examples of user devices that may implemental a portal include, without limitation, personal computers, laptops, and mobile devices (such as smartphones, blackberries, PDAs, tablet computers, etc.). For example, a portal may be implemented over a web browser or a mobile application installed on the user device. Only one server, one clinical portal 114, and one pharmacy portal 124 are shown in FIG. 1 to avoid complicating the drawing; the system 100 can support multiple servers and multiple clinical portals and pharmacy portals.

In FIG. 1, a patient 116 is examined by a medical professional 118, who has access to the clinical portal 114. The patient may be subject to a disease that has a known progression, and consults the medical professional 118. The medical professional 118 makes measurements from the patient 116 and records these measurements over the clinical portal 114. For example, the medical professional 118 may draw a sample of the blood of the patient 116, and may measure a concentration of a biomarker in the blood sample.

In general, the medical professional 118 may make any suitable measurement of the patient 116, including lab results such as concentration measurements from the patient's blood, urine, saliva, or any other liquid sampled from the patient. The measurement may correspond to observations made by the medical professional 118 of the patient 116, including any symptoms exhibited by the patient 116. For example, the medical professional 118 may perform an examination of the patient gather or measure patient-specific factors such as sex, age, weight, race, disease stage, disease status, prior therapy, other concomitant diseases and/or other demographic and/or laboratory test result information. More specifically, this involves identifying patient characteristics that are reflected as patient factor covariates within the mathematical model that will be used to predict the patient's response to a drug treatment plan. For example, if the model is constructed such that it describes a typical patient response as a function of weight and gender covariates, the patient's weight and gender characteristics would be identified. Any other characteristics may be identified that are shown to be predictive of response, and thus reflected as patient factor covariates, in the mathematical models. By way of example, such patient factor covariates may include weight, gender, race, lab results, disease stage and other objective and subjective information.

Based on the patient's measurement data, the medical professional 118 may make an assessment of the patient's disease status, and may identify a drug suitable for administering to the patient 116 to treat the patient 116. The clinical portal 114 may then transmit the patient's measurements, the patient's disease status (as determined by the medical professional 118), and an identifier of the drug over the network 102 to the server 104, which uses the received data to select one or more appropriate computational models from the models database 106. The appropriate computational models are those that are determined to be capable of predicting the patient's response to the administration of the drug. The one or more selected computational models are used to determine a recommended set of planned dosages of the drug to administer to the patient, and the recommendation is transmitted back over the network 102 to the clinical portal 114 for viewing by the medical professional 118.

Alternatively, the medical professional 118 may not be capable of assessing the patient's disease status or identify a drug, and either or both of these steps may be performed by the server 104. In this case, the server 104 receives the patient's measurement data, and correlates the patient's measurement data with the data of other patients in the patient database 106a. The server 104 may then identify other patients who exhibited similar symptoms or data as the patient 116 and determine the disease states, drugs used, and outcomes for the other patients. Based on the data from the other patients, the server 104 may identify the most common disease states and/or drugs used that resulted in the most favorable outcomes, and provide these results to the clinical portal 114 for the medical professional 118 to consider.

As is shown in FIG. 1, the database 106 includes a set of four databases including a patient database 106a, a disease database 106b, a treatment plan database 106c, and a models database 106d. These databases store respective data regarding patients and their data, diseases, drugs, dosage schedules, and computational models. In particular, the patient database 106a stores measurements taken by or symptoms observed by the medical professional 118. The disease database 106b stores data regarding various diseases and possible symptoms often exhibited by patients infected with a disease. The treatment plan database 106c stores data regarding possible treatment plans, including drugs and dosage schedules for a set of patients. The set of patients may include a population with different characteristics, such as weight, height, age, sex, and race, for example. The models database 106d stores data regarding a set of computational models that may be used to describe PK, PD, or both PK and PD changes to a body. One example of a PK/PD model is described in relation to FIG. 2 and EQS. 1-16.

Any suitable mathematical model may be stored in the models database 106d, such as in the form of a compiled library module, for example. In particular, a suitable mathematical model is a mathematical function (or set of functions) that describes the relationship between a dosing regimen and the observed patient exposure and/or observed patient response (collectively "response") for a specific medication. Accordingly, the mathematical model describes response profiles for a population of patients. Generally, development of a mathematical model involves developing a mathematical function or equation that defines a curve that best "fits" or describes the observed clinical data, as will be appreciated by those skilled in the art.

Typical models also describe the expected impact of specific patient characteristics on response, as well as quantify the amount of unexplained variability that cannot be accounted for solely by patient characteristics. In such models, patient characteristics are reflected as patient factor covariates within the mathematical model. Thus, the mathematical model is typically a mathematical function that describes underlying clinical data and the associated variability seen in the patient population. These mathematical functions include terms that describe the variation of an individual patient from the "average" or typical patient, allowing the model to describe or predict a variety of outcomes for a given dose and making the model not only a mathematical function, but also a statistical function, though the models and functions are referred to herein in a generic and non-limiting fashion as "mathematical" models and functions.

It will be appreciated that many suitable mathematical models already exist and are used for purposes such as drug product development. Examples of suitable mathematical models describing response profiles for a population of patients and accounting for patient factor covariates include PK models, PD models, hybrid PK/PD models, and exposure/response models. Such mathematical models are typically published or otherwise obtainable from medication manufacturers, the peer-reviewed literature, and the FDA or other regulatory agencies. Alternatively, suitable mathematical models may be prepared by original research. Moreover, as is described in the '545 application, a Bayesian model averaging approach may be used to generate a composite model to predict patient response when multiple patient response models are available, though a single model may also be used.

In particular, the output of the PK/PD model corresponds to a dosing regimen or schedule that achieves an optimal target level for a physiological parameter of the patient 116. The PK/PD model provides the optimal target level as a recommendation specifically designed for the patient 116, and has verified that the optimal target level is expected to produce an effective and therapeutic response in the patient 116. In the example shown and described in relation to FIG. 2, the physiological parameter corresponds to a concentration of a drug in the patient's blood, though in general, the physiological parameter may correspond to any number of measurements from a patient. When the drug is infliximab, for example, it may be desirable to measure the drug concentration (and predict the drug concentration using a PK model, as is described in detail below) and other measurable units (that may be predicted by a PD model, for example), such as C reactive protein, endoscopic disease severity, and fecal calprotectin. Each measurable (e.g., the drug concentration, C reactive protein, endoscopic disease severity, and fecal calprotectin) may involve one or more PK and/or PD models. The interaction between PK and PD models may be particularly important for a drug like infliximab, in which patients with more severe disease clear the drug faster (modeled by higher clearance from a PK model, as is explained in detail below). One goal of the drug infliximab may be to normalize C reactive protein levels, lower fecal calprotectin levels, and achieve endoscopic remission.

In one example, the medical professional 118 may assess the likelihood that the patient 116 will exhibit a therapeutic response to a particular drug and dosing regimen. In particular, this likelihood may be low if several dosing regimens of the same drug have been administered to the patient, but no measurable response from the patient is detected. In this case, the medical professional 118 may determined that it is unlikely that the patient will response to further adjustments to the dose, and other drugs may be considered. Moreover, as is described in detail below, a confidence interval may be assessed for the predicted model results (e.g., the predicted exposure to the drug (as provided by the PK model) and the predicted response of the body to the presence of the drug (as provided by the PD model). As data is collected from the patient 116, the confidence interval gets narrower, and is indicative of a more trustworthy result and recommendation.

Importantly, the systems and methods of the present disclosure allow for the simultaneous interaction and fit of the PK and PD models. The PD model is used to identify an individualized target level, and the PK model is used to provide individualized dosing recommendations based on the individualized target level. Moreover, by simultaneously fitting both a PK model and a PD model, the two models that predict drug level and therapeutic response are allowed to interact in a manner that is more physiologically realistic than other models.

Often, the medical professional 118 may be a member or employee of a medical center. The same patient 116 may meet with multiple members of the same medical center in various roles. In this case, the clinical portal 114 may be configured to operate on multiple user devices. The medical center may have its own records for the particular patient. In some implementations, the present disclosure provides an interface between the computational models described herein and a medical center's records. For example, any medical professional 118, such as a doctor or a nurse, may be required to enter authentication information (such as a username and password) or scan an employee badge over the user interface 112 to log into the system provided by the clinical portal 114. Once logged in, each medical professional 118 may have a corresponding set of patient records that the professional is allowed to access.

In some implementations, the patient 116 interacts with the clinical portal 114, which may have a patient-specific page or area for interaction with the patient 116. For example, the clinical portal 114 may be configured to monitor the patient's treatment schedule and send appointments and reminders to the patient 116. Moreover, one or more devices (such as smart mobile devices or sensors) may be used to monitor the patient's ongoing physiological data, and report the physiological data to the clinical portal 114 or directly to the server 104 over the network 102. The physiological data is then compared to expectations, and deviations from expectations are flagged. Monitoring the patient's data on a continual basis in this manner allows for possible early detection of deviations from expectations of the patient's response to a drug, and may indicate the need for early intervention or alternate therapy.

As described herein, the measurements from the patient 116 that are provided into the computational model may be determined from the medical professional 118, directly from devices monitoring the patient 116, or a combination of both. Because the computational model predicts a time progression of the disease and the drug, and their effects on the body, these measurements may be used to update the model parameters, so that the treatment plan (that is provided by the model) is refined and corrected to account for the patient's specific data.

In some implementations, it is desirable to separate a patient's personal information from the patient's measurement data that is needed to run the computational model. In particular, the patient's personal information may be protected health information (PHI), and access to a person's PHI should be limited to authorized users. One way to protect a patient's PHI is to assign each patient to an anonymized code when the patient is registered with the server 104. The code may be manually entered by the medical professional 118 over the clinical portal 114, or may be entered using an automated but secure process. The server 104 may be only capable of identifying each patient according to the anonymized code, and may not have access to the patient's PHI. In particular the clinical portal 114 and the server 104 may exchange data regarding the patient 116 without identifying the patient 116 or revealing the patient's PHI.

The generation or selection of the code may be performed in a similar manner as is done for credit card systems. For example, all access to the system may be protected by an application programming interface (API) key. Moreover, when the medical professional 118 is part of a medical center, the medical center's connection to the network 102 over the clinical portal 114 may have enhanced security systems in compliance with HIPAA. As an example, a single administrative database may define access in a manner that ensures that members of one team (e.g., one set of medical professionals, for example) are prohibited from viewing records associated with another team. To implement this, each end-user application may be issued a single API key that specifies which portions of a database may be accessed.

In some implementations, multiple levels of clinician interaction with the portal are configured. For example, some medical professionals, upon logging into the clinical portal 114, may have access that only allows them to view the patient's data. Another level of access may allow the medical professional 118 to view the patient's data as well as enter measurement and observation data regarding the patient 116. A third level of access may allow the medical professional 118 to view and update the patient's data, as well as prescribe a treatment for the patient 116 or otherwise update the patient's treatment plan or dosing schedule.

Different levels of access may be set for different types of users. For example, a user who is a system administrator for the clinical portal 114 may be able to grant or rescind access to the system to other users, but does not have access to any patient records. As another example, a prescriber may be allowed to modify a particular patient's treatment plan and has read and write access to patient records. A reviewer may have just read-only access to patient records, and can only view a patient's treatment plan. A data manager may have read and write access to the patient records, but may not be allowed to modify a patient's treatment plan.

In some implementations, the clinical portal 114 is configured to communicate with the pharmacy portal 124 over the network 102. In particular, after a dosing regimen is selected to be administered to the patient 116, the medical professional 118 may provide an indication of the selected dosing regimen to the clinical portal 114 for transmitting the selected dosing regimen to the pharmacy portal 124. Upon receiving the dosing regimen, the pharmacy portal 124 may display the dosing regimen and an identifier of the medical professional 118 over the user interface 122, which interacts with the pharmacist 128 to fulfill the order.

In some implementations, recommendations or custom orders for drug amounts is provided to drug manufacturers (not shown), who may have access to the network 102. Manufacturers of drugs may only produce certain drugs at set amounts or volumes, which may correspond to recommended dosage amounts for the "typical" patient. This may be especially true for expensive drugs. However, as is described herein, the optimal amount or dosing schedule of a drug for a specific patient may be different for different patients. Moreover, some drugs have expiration dates or have decreased efficacy over time as the drug sits on the shelf. Thus, if it is desirable to administer the optimal amount of drug according to a recommended dosing regimen, then this could potentially lead to drug wastage at least because the optimal amount may not correspond to an integer multiple of the set amount that is produced by the manufacturer.

One way for this problem to be mediated is to provide information to the drug manufacturer reflective of the recommended dosing regimen ahead of time, so that the drug manufacturer can produce custom sized orders for certain medications at the desired times according to the regimen. In this manner, the present disclosure allows for drugs to be freshly produced in the desired amounts at a time that is as close to the administration time as possible.

Moreover, clinical phase IV drug trials are often limited due to the expensive cost of the drugs. The present disclosure provides a way for data regarding a subject's specific response to a drug to be fed back into the models to adequately capture the subject's specific data. The present disclosure provides an automated method of computing a recommended dosage schedule that is deterministic. The dosage schedule can be supplied economically and quickly in a secure manner (e.g., without revealing the patient's PHI) to the drug manufacturer, who may then manufacture customized orders, thereby saving on cost and leading to reduced drug wastage. Moreover, the manufacturer of the drug may be interested in the tested efficacy of the drug, and may be able to adjust the amounts of the drug that are produced and/or the production timeline to accommodate various dosing regimens.

In addition, to the extent that a drug manufacturer's timeline is limited by certain factors, the present disclosure is capable of providing recommended dosing regimens within the limits of the drug manufacturer. For example, for technological and/or economical reasons, the drug manufacturer may only be able to produce a drug in set quantities. Because a dosing regimen often involves two parameters (namely, an amount of a drug and a time at which to administer the drug), the recommended dosing regimen provided by the system 100 may be modified accordingly to accommodate the drug manufacturer's limits.

As is shown in FIG. 1, the server 104 is a device (or set of devices) that is remote from the clinical portal 114. Depending on the computational power of the device that houses the clinical portal 114, the clinical portal 114 may simply be an interface that primarily transfers data between the medical professional 118 and the server 104. Alternatively, the clinical portal 114 may be configured to locally perform any or all of the steps described to be performed by the server 104, including but not limited to receiving patient symptom and measurement data, accessing any of the databases 106, running one or more computational models, and providing a recommendation for a dosage schedule based on the patient's specific symptom and measurement data. Moreover, while FIG. 1 depicts the patient database 106a, the disease database 106b, the treatment plan database 106c, and the models database 106d as being entities that are separate from the server 104, the clinical portal 114, or the pharmacy portal 124, one of ordinary skill in the art will understand that any or all of the databases 106 may be stored locally on any of the devices or portals described herein, without department from the scope of the present disclosure.

Figure 2:
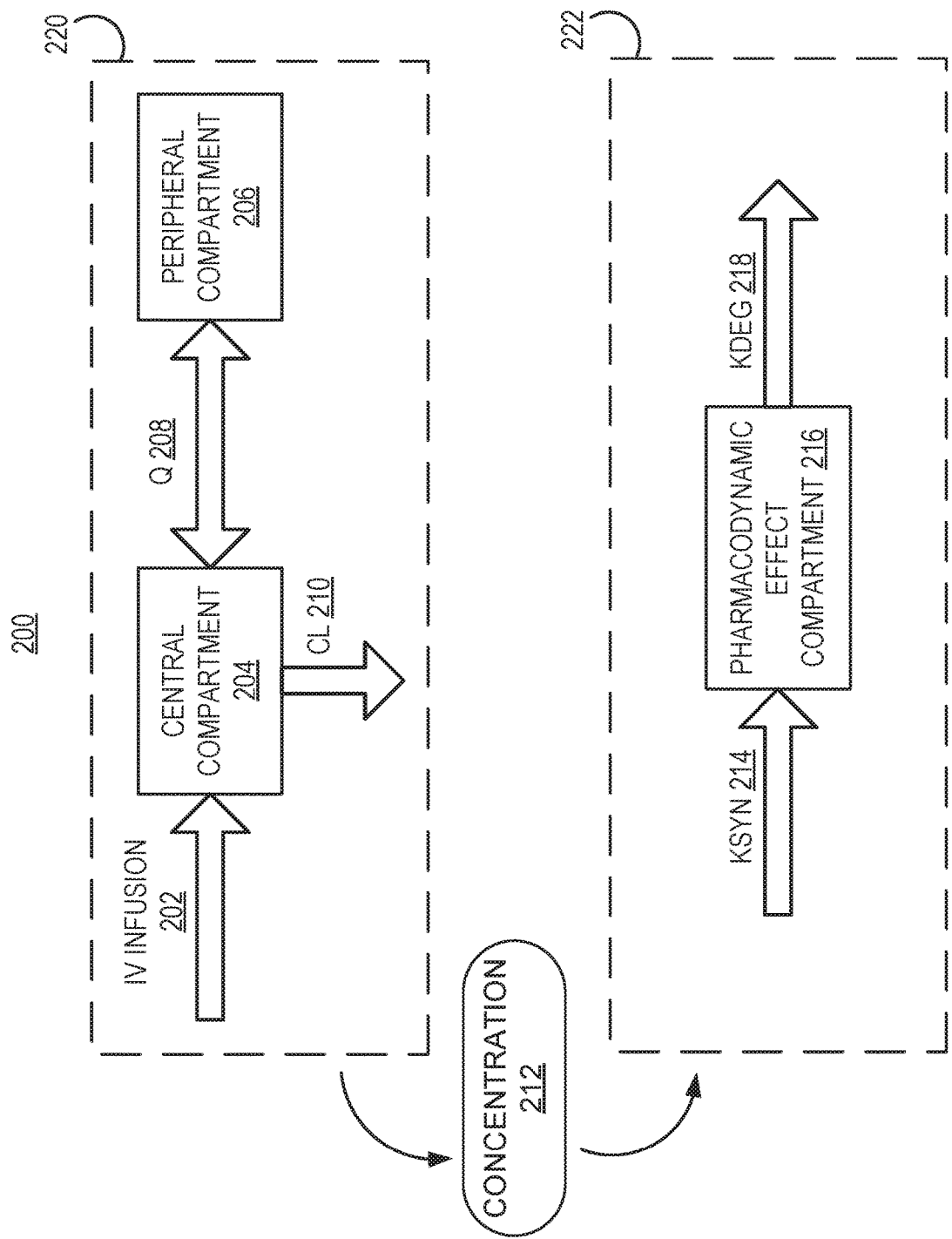
FIG. 2 is a block diagram of a pharmacokinetic/pharmacodynamic model that can be used to determine a target level of a physiological parameter for a specific patient and provide a suggested dosing regimen, according to an illustrative implementation.

FIG. 2 is a block diagram 200 of an illustrative compartmental model for pharmacokinetics and pharmacodynamics. A compartmental model generally describes the result when a drug enters a body, which is represented as one or more compartments, which may represent one or more organs or tissues within the body. Specifically, the drug enters the body via a site of administration and enters a central compartment. From the central compartment, the drug may be exchanged with one or more peripheral compartments that represent distribution of the drug to other regions of the body. The drug may also be eliminated from the central compartment via metabolism or excretion processes. The movement of the drug (into and out of the central compartment and any peripheral compartments) may be represented by using transfer rate constants For example, a PK model 220 for infliximab (IFX) may include the two compartments shown in FIG. 2, which includes a central compartment 204 and a peripheral compartment 206. The central compartment 204 may generally represent blood circulation in an organism and corresponds to a relatively rapid distribution. For example, the central compartment may represent organs and systems within an organism that have a well-developed blood supply, such as the liver or kidney. In contrast, the peripheral compartment 206 may represent organs or systems that have lower blood flow, such as muscle, lean tissue, and fat.

In addition to the two compartments in the PK model 220, FIG. 2 also depicts input flows and output flows into and out of the compartments. In particular, the IV infusion 202 corresponds to a flow rate of entrance of the drug into the body via the site of administration and into the central compartment 204. The clearance (CL) 210 corresponds to an exit flow rate out of the central compartment 204, and may be representative of an amount of drug that is flushed out of the system, such as via metabolism or excretion processes.

The inter-compartmental clearance (Q) 208 corresponds to a flow rate between the central compartment 204 and the peripheral compartment 206, and represents distribution of the drug between organs with higher blood flow and organs with lower blood flow.

For IFX, the following system of equations may be used to represent the PK model.

$$CL = \left(\theta_1 * \left(\frac{\text{Weight}}{70}\right)^{\theta_6} * \left(\frac{ALB}{4}\right)^{\theta_{10}} * \left(\frac{AST}{30}\right)^{\theta_{11}} * (1 + \theta_{12} * IRP)\right) * \exp(\eta_1) \quad \text{EQ. 1}$$

$$V1 = \theta_2 * \left(\frac{\text{Weight}}{70}\right)^{\theta_7} * \exp(\eta_2) \quad \text{EQ. 2}$$

$$Q = \left(\theta_3 * \left(\frac{\text{Weight}}{70}\right)^{\theta_8} * \left(\frac{ALB}{4}\right)^{\theta_{13}}\right) * \exp(\eta_3) \quad \text{EQ. 3}$$

$$V2 = \theta_4 * \left(\frac{\text{Weight}}{70}\right)^{\theta_9} * \exp(\eta_4) \quad \text{EQ. 4}$$

In the above set of equations, the set of values for $\theta_i$ denotes a vector of fixed-effect parameters that represent structural parameters of the model. The parameter "weight" represents the weight of the patient in kilograms, ALB represents a level of albumin in grams per deciliter, AST represents a level of aspartate aminotransferase in international units per liter, and IRP represents Immune Response Positive. These parameters are examples of physiological parameters that are measurable directly from the patient. As used in EQ. 1, the value for IRP is indicative of whether the patient has developed antibodies against the drug IFX. If so, this increases the clearance of the drug out of the central compartment 204. The parameter V1 corresponds to the volume of distribution of the central compartment 204, and the parameter V2 corresponds to the volume of distribution of the peripheral compartment 206. The set of values for $\eta_i$ represents between-subject variability for the clearance ($\eta_1$), the volume V1 ($\eta_2$), the inter-compartmental clearance Q ($\eta_3$), and the volume V2 ($\eta_4$). Generally, the values $\eta_i$ represent the unexplained random variability that is not captured by patient factors.

EQS. 1-4 represent a two-compartmental PK model for the distribution of IFX in a body, and the patient-specific parameters that are not readily measurable are solved for based on measurable patient parameters. In particular, none of the parameters in the above set of equations may be readily measurable from a patient, but these parameters may be inferred from measurements of concentration of a drug in a patient's blood.

For example, the concentration time profile of IFX in a patient's blood may be measured and then compared to a predicted time profile of IFX using the following set of equations. The parameters above, including CL, V1, Q, V2, $\theta_i$, and $\eta_i$, may then be fit to result in a predicted concentration time profile that resembles the measured concentration time profile.

$$\frac{dA(1)}{dt} = -\left(\frac{CL}{V1}\right)*A(1) - \left(\frac{Q}{V1}\right)*A(1) + \left(\frac{Q}{V2}\right)*A(2) \quad \text{EQ. 5}$$

$$\frac{dA(2)}{dt} = \left(\frac{Q}{V1}\right)*A(1) - \left(\frac{Q}{V2}\right)*A(2) \quad \text{EQ. 6}$$

In EQS. 5 and 6 above, A(1) denotes an amount of IFX in the central compartment 204, and A(2) denotes an amount of IFX in the peripheral compartment 206. In particular, EQ. 5 represents the net flow rate of the drug IFX into the central compartment 204, after accounting for the clearance 210, and the inter-compartmental clearance 208. As is shown in EQ. 5, the flow rate of the IV infusion 202 is not included. However, it will be understood that EQ. 5 may be modified to include the flow rate of input of the drug during the time(s) of infusion. For example, the right hand side of EQ. 5 may be modified to include a flow rate parameter RO, which is set to the input flow rate of the drug during infusion time, and zero when no infusion takes place. The $$\left(\frac{CL}{V1}\right)*A(1) \text{ and } \left(\frac{Q}{V1}\right)*A(1)$$

terms in EQ. 5 are negative because these correspond to flow rates of IFX exiting the central compartment 204, while the term $$\left(\frac{Q}{V2}\right)*A(2)$$

corresponds to an input flow rate of IFX from the peripheral compartment 206. Similarly, EQ. 6 represents the net flow rate of IFX into the peripheral compartment 206, after accounting for the inter-compartmental clearance 208 that enters the peripheral compartment 206 (corresponding to the positive term $$\left(\frac{Q}{V1}\right)*A(1))$$

and that exits the peripheral compartment 206 (corresponding to the negative term $$\left(\frac{Q}{V2}\right)*A(2)).$$

The initial conditions may be set such that both A(1) and A(2) are initially zero (before administration of any IFX). As discussed above, EQS. 1-6 may be used to predict a concentration time profile of IFX in the central compartment 204. The concentration time profile may be represented as $$\frac{A(1)(t)}{V1},$$

or the amount of IFX in the central compartment 204 as a function of time, divided by the volume of the central compartment 204. The profile $$\frac{A(1)(t)}{V1}$$

may be referred to herein as a predicted concentration time profile, because the profile results from model predictions, and not from direct measurements.

To determine whether the model predictions and values for the model parameters are reasonable, the predicted concentration time profile is compared to a measured concentration time profile. The measured concentration time profile may be directed measured by sampling a patient's blood at different times, and measuring the concentration of IFX in the blood. An optimization technique may be performed to compute estimates for CL, V1, Q, and V2 by determining values for the set of theta values $\theta_i$, and estimating difference parameter values for the set of eta values $\eta_i$ (which represent unexplained variability), that minimize the error between the measured concentration time profile and the predicted concentration time profile.

$$\text{Concentration}(t) = \frac{A(1)(t)}{V1} * \exp(\varepsilon_1) \qquad \text{EQ. 7}$$

In EQ. 7, the parameter concentration(t) corresponds to the measured concentration of IFX in a patient's blood as a function of time, while the values for A(1)(t) and V1 are provided from the two-compartmental PK model. The parameter $E_1$ corresponds to a residual error that is representative of measurement error. The optimization may be performed to minimize the residual error between the measurements and predictions. As is shown in FIG. 2, the predicted concentration 212 is provided by the PK model 220 to a PD model 222.

In contrast to the above-described PK model 220, a PD model 222 predicts the physiological and biochemical effects of a drug on a body. In particular, the effect of a drug and the drug's concentration may be represented with a sigmoidal curve. In this case, for drug concentrations below a first threshold, the effect of the drug may be minimal and may have little to no effect. For drug concentrations above a second threshold (higher than the first threshold), the effect of the drug may be maximal, and higher concentration would not result in much increased effect. This maximal drug effect is represented by a unitless parameter Emax, which may be defined as in EQ. 8.

$$E\text{max} = \theta_{14} * \exp(\eta_5) \qquad \text{EQ. 8}$$

Moreover, the concentration of a drug that is between the first and second thresholds, and that produces an effect of the drug at half of the maximal effect Emax, is referred to as EC50 (having units of amount/volume), and is described in EQ. 9.

$$EC50 = \theta_{15} * \exp(\eta_6) \qquad \text{EQ. 9}$$

The concentration that achieves half the maximal response (EC50) represents a key parameter in the PD model and may be used to determine appropriate drug exposure to maintain therapeutic response. Importantly, the particular value for EC50 for different patients may be different, as is denoted with the between subject variability parameter $r_{16}$. This indicates that the target concentration necessary to achieve maximal meaningful clinical effect for different patients may be different, and should therefore be estimated individually for each patient. In some implementations, the target concentration does not correspond to the concentration that achieves half the maximal response. In particular, higher or lower values may be used, and are dependent on the particular goal to be achieved. For example, if a drug lowers blood pressure, this may mean that the maximal response of the body to the drug means that the blood pressure is reduced to zero. In this case, a drug concentration that achieves half of this maximal response may be too severe, and a much lower target value for the drug concentration may be used instead. However, even in this case, knowledge of the maximal response and what the value of the concentration is that achieves half the maximal response may be important in determining the target concentration. By estimating the EC50 parameter on a patient-by-patient basis, the systems and methods of the present disclosure use a computational method of determining the relevant target concentration of a drug in an individual that is likely to produce a therapeutic response.

In a turnover PD model, parameters are used to represent a base amount of a PD marker prior to drug administration (e.g., Base) and a synthesis rate of the PD marker (e.g., Ksyn 214, having units amount/time).

$$\text{Base} = \theta_{16} * \exp(\eta_7) \qquad \text{EQ. 10}$$

$$K\text{syn} = \theta_{17} * \exp(\eta_8) \qquad \text{EQ. 11}$$

Base corresponds to the PD response prior to the first administration of drug, and Ksyn 214 is the rate of formation of the PD marker. Moreover, in the untreated state, the parameters Base and Ksyn are related to each other according to EQ. 12, which describes a ratio of Ksyn and Base as a degradation rate of the PD marker (e.g., Kdeg 218, having units 1/time), since the undisturbed baseline value is the ratio of formation and degradation of the PD marker.

$$K\text{deg} = \frac{K\text{syn}}{\text{Base}} \qquad \text{EQ. 12}$$

In particular, the parameters described in relation to EQS. 8-12 are used to model C reactive protein, which is one of the markers of disease activity that may be tracked when IFX is used. In general, the same parameters in EQS. 8-12 may be used to model C reactive protein with any other suitable drug. Moreover, one of ordinary skill in the art will understand that other parameters that track any marker in relation to any drug or pharmaceutical may be used without departing from the scope of the present disclosure. The example PD model used herein is a turnover model. However, generally, any suitable PD model may be used without departing from the scope of the present disclosure. The specific type of PD model may depend on the drug and the PD marker. Examples of types of PD models are not limited to turnover models and include direct effect PD models, link effect PD models, indirect effect or turnover PD models, transit PD models, or any suitable combination thereof.

In the PD model 222 shown in FIG. 2, a pharmacodynamics effect compartment 216 is depicted as having an input Ksyn 214 and an output Kdeg 218. In the PD model 222, the overall effect of a drug on a body may be represented as in EQ. 13, where the values for Concentration, Emax, and EC50 are as described in relation to EQS. 7, 8, and 9, respectively.

$$\text{Effect} = \frac{E\text{max} * \text{Concentration}}{EC50 + \text{Concentration}} \qquad \text{EQ. 13}$$

Moreover, the PD effect compartment 216 represents an amount of clearance of the biomarker that is mediated by the presence of the drug. In particular, EQ. 14 describes a differential equation for the flow rate of the biomarker or PD endpoint (e.g., a quantity that is measurable on a patient and is indicative of a PD response A(3)) within the PD effect compartment 216, and relates to the synthesis rate Ksyn, the degradation rate Kdeg, and the overall effect of the drug Effect to the measured level of biomarker.

$$\frac{dA(3)}{dt} = Ksyn - Kdeg * A(3) * (1 + \text{Effect}) \qquad \text{EQ. 14}$$

In particular, the concentration of the drug (from EQ. 7) (predicted by the model) is used to drive the response of the PD model by first providing the individually estimated concentration into EQ. 13 and EQ 14, which are updated simultaneously to determine the overall effect of the drug, and to determine a predicted time profile of the response A(3). In general, the predicted concentration 212 may be provided to the PD model 222 rather than the measured concentration profile, at least because the predicted concentration provides a smoother function to fit to the PD model 222. An initial condition for the PD compartment for the response A(3) may be set to the Base parameter, which represents the PD response measurement prior to the initiation of treatment.

Then, in a similar manner as described in relation to EQ. 7, the time profile of the predicted value of the PD marker A(3) is fit to the patient's measured Response, as is shown in EQ. 15, where $\epsilon_2$ represents the residual error for the PD evaluation and corresponds to measurement error.

$$\text{Response} = A(3) * \exp(\epsilon_2) \qquad \text{EQ. 15}$$

The optimization may be performed to minimize the residual error between the measurements and predictions. In particular, the patient's measured Response to the drug IFX may correspond to a laboratory measurement of C reactive protein or fecal calprotectin. Alternatively or additionally, the patient's measured Response may include a categorical observation, such as endoscopic remission, which may indicate one of various states, including progressive disease, stable disease, partial response, or complete response.

With at least some drugs, the response of the system (as modeled by the PD model) affects the amount of the drug that remains in the system or is flushed out (as modeled by the PK model). Thus, the PK model (as described in relation to EQS. 1-7) may be combined with the PD model (as described in relation to EQS. 8-15) to form a PK/PD model that describes the interrelation between the two models. To combine the two models, the equations above may be modified to include the effect of the pharmacodynamics on the pharmacokinetics.

In one example, this is performed by updating the clearance 210 (from the PK model) to reflect the response A(3) (from the PD model), as is shown in EQ. 16.

$$CLT = CL + A(3) * \exp(-K * t) \qquad \text{EQ. 16}$$

The parameter CLT corresponds to a total clearance metric and is represented as an addition between the original PK clearance parameter (CL) and the PD estimate for the PD marker A(3), modified by a rate constant K. In this example, the rate constant K reflects the diminishing effect of the PD response on CL over time. Even though the value for the amount A(3) is also generally expected to diminish with time (due to the presence of the drug), the rate constant K represents a separate effect, as the PD endpoint approaches normal ranges. In particular, as the patient heals and the disease is eliminated, the total clearance CLT approaches the PK clearance CL.

One example computational model for IFX is described herein for illustrative purposes, but in general, one of ordinary skill in the art will understand that the systems and methods of the present disclosure are applicable to any computational model that involves both pharmacokinetics and pharmacodynamics to estimate a target value for a physiological parameter. In particular, a two-compartment model has been shown and described in relation to FIG. 2, but in general, any number of compartments may be used without departing from the scope herein. In particular, the PK model may include a non-compartmental component, or be a single-compartment, multi-compartmental, or any other suitable PK model. Moreover, depending on the particular disease, disease status, and the drug, different mathematical functions and equations that describe the impact of the PD marker on the body may be used in the models, without departing from the scope of the present disclosure.

Importantly, the above IFX example illustrates that not only do the systems and methods of the present disclosure provide a recommended dosing regimen to achieve a particular target level for a physiological parameter (e.g., concentration level of a drug or biomarker in blood), but the present disclosure also is able to evaluate whether the particular target level would be effective for a specific patient exhibiting specific characteristics and responses. As described above, the target level of concentration EC50 (which is derived from the individual) needed to achieve an effective response from the patient is estimated specifically for a particular patient. The estimate for EC50 may be periodically updated, such as whenever any additional patient measurement data is recorded, or when a threshold amount of additional patient measurement data is received. For example, depending on the computational complexity of the models used, it may be undesirable to re-run the computational models whenever any measurement is taken from the patient. Instead, it may be desirable to wait until a full set of measurements is taken, or until enough data is collected that deviates from what is expected. As used in the above example, the target concentration level corresponds to a concentration level that would cause the patient to respond with a clinically meaningful effect. In general, the target concentration level may correspond to any suitable fraction of a maximal effect, without departing from the scope of the present disclosure.

Figure 3:
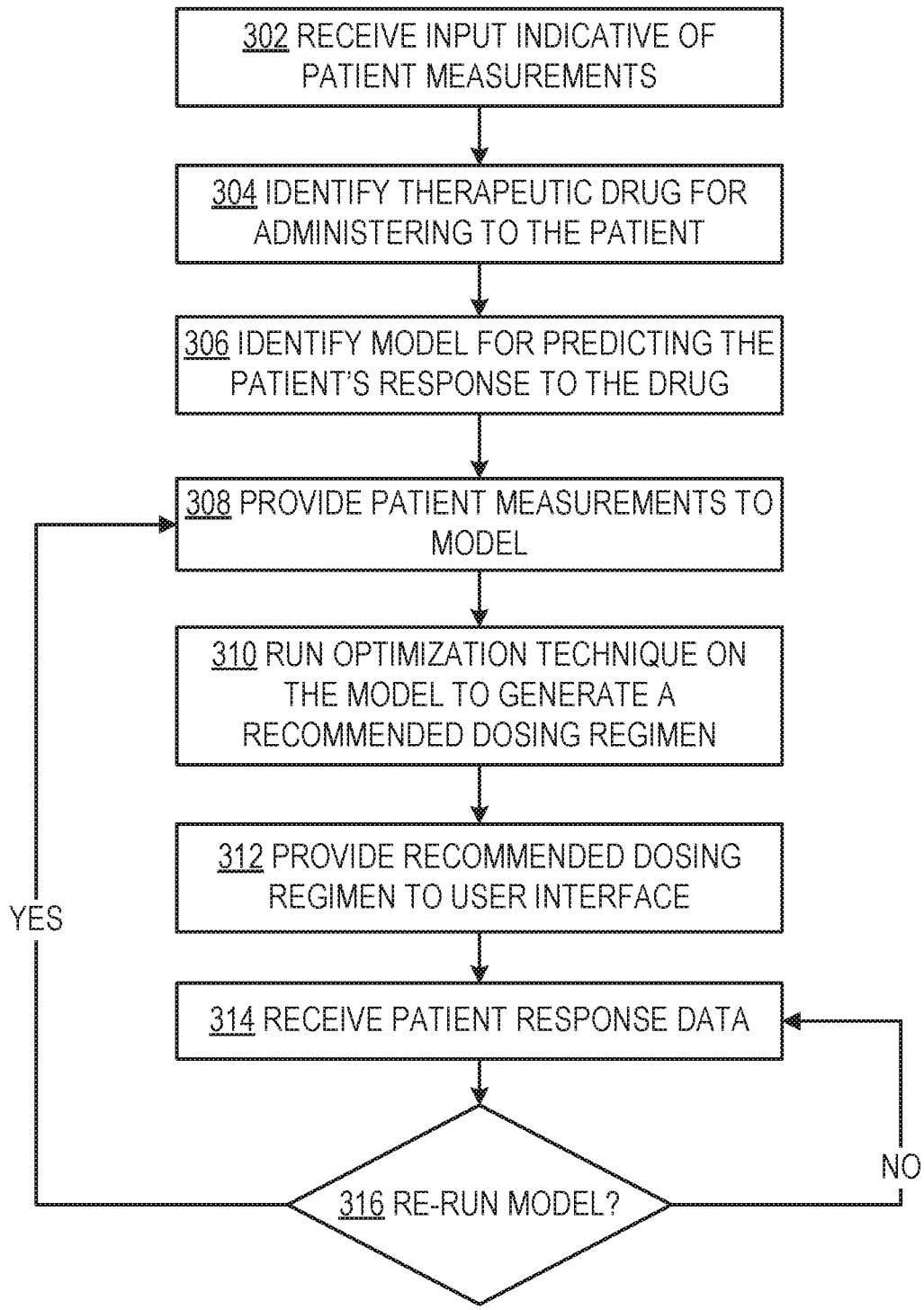
FIG. 3 is a flowchart of a method used by a computerized system to provide a recommended dosing regimen for a specific patient, according to an illustrative implementation.

FIG. 3 is a flowchart of a method 300 that may be implemented by the system 100 to provide a recommended treatment plan to a specific patient, where the treatment plan is designed particularly for the specific patient, based on the patient's measurements and data. In general, the method 300 provides an analysis of the patient's specific data and determines an appropriate treatment plan or dosing regimen suitable for recommendation to the patient. An overview of the method 300 will first be provided, followed by illustrations of various implementations of the steps of the method. As shown, the method 300 generally includes the steps of receiving an input indicative of the patient's measurements (step 302). The patient's measurements may include a disease status of the patient and/or a history of the patient's responses to dosing regimens of medications that have been previously administered to the patient. Based on the patient's measurements, a therapeutic drug for administering to the patient is identified (step 304). The method further includes identifying a model for predicting the patient's response to the drug (step 306), and providing the patient's measurements to the model (step 308). Then, an optimization technique on the model is run to generate a recommended dosing regimen for the specific patient (step 310), and the recommended dosing regimen is provided to a user interface (step 312). After the recommended dosing regimen (or a variant of the recommended dosing regimen) is administered to the patient, additional data may be recorded from the patient, and data indicative of the patient's response to the administered dosing regimen is received (step 314).

Based on the patient's response data, it is determined whether to re-run the model (decision block 316). If so, the method 300 returns to step 308 to provide the patient's updated measurements to the model, and if not, the method 300 ends until additional patient response data is received to warrant a re-running of the model.

At step 302, an input indicative of patient measurements is received. For example, as was described in relation to FIG. 1, the medical professional 118 makes measurements from the patient 116. The medical professional 118 may draw a sample of the blood of the patient 116, and may measure a concentration of a biomarker in the blood sample. In general, the medical professional 118 may make any suitable measurement of the patient 116, including lab results such as concentration measurements from the patient's blood, urine, saliva, or any other liquid sampled from the patient. The measurement may include observations made by the medical professional 118 of the patient 116, including any symptoms exhibited by the patient 116. For example, the medical professional 118 may perform an examination of the patient gather or measure patient-specific factors such as sex, age, weight, race, disease stage, disease status, prior therapy, other concomitant diseases and/or other demographic and/or laboratory test result information.

At step 304, a therapeutic drug is identified for administering to the patient. The medical professional 118 may already know which drug should be administered to the patient 116, and so may provide the name or other identifier of the drug to the clinical portal 114. The drug may be determined based on an assessment of the patient's disease status.

At step 306, a model is identified for predicting the patient's response to the drug identified at step 304. In particular, one or more appropriate computational models may be selected from the models database 106. As is described in the '545 application, a Bayesian model averaging approach may be optionally used to generate a composite model to predict patient response. The averaging may be used when multiple patient response models are available, and corresponding weights may be assigned to each patient response model, where the weights correspond to a level of confidence in each model. In an example, multiple PK and/or PD models are tested, and those models that have better performance (e.g., by fitting the measurement data better than other models) may be determined to be more likely than other models, and accordingly are assigned higher weights or ranks. As an example, there may be multiple PK models or multiple PD models, and the response of each model may be averaged across the multiple models. As an example, a single PD model may include multiple paths, where each path describes a causal relationship between the administration of the drug and its effect on the patient's body. For example, one effect of the drug on the patient's body is that the patient may improve, while another possible effect is that the patient may not improve or worsen. In this case, averaging may occur over the various paths of the model. In general, the "composite" model may refer to the averaged model when multiple patient response models are available, to a single model, or to one of several possible models describing different paths or trajectories.

At step 308, the patient measurements received at step 302 are provided as inputs into the model identified at step 306. In particular, as was described in the example shown in FIG. 2, various parameters of the computational model may be set in accordance with the patient measurements. For example, the patient's weight, ALB, AST, and IRP may be values that are readily measurable and input into EQS. 1-4.

Moreover, the patient's concentration time profile may be measured and used as the parameter "concentration" in EQ. 7. The example described in relation to FIG. 2 is shown for illustrative purposes only, and one will understand that any suitable measurements may be made and provided as input to a computational model.

At step 310, an optimization technique is run on the model to generate a recommended dosing regimen. In particular, as was described in the '545 application, a Bayesian forecasting process may be used to test various dosing regimens for the patient 116 as a function of the patient's specific characteristics accounted for as patient factor covariates within the models, and the composite mathematical model. This forecasting involves evaluating dosing regimens based on predicted responses for a typical patient with the patient-specific characteristics. Generally, Bayesian forecasting involves using mathematical model parameters to forecast the likely response that a specific patient will exhibit with various dosing regimens. Notably, forecasting allows for determination of a likely patient response to a proposed dosing regimen before actual administration of a proposed dosing regimen. Accordingly, the forecasting can be used to test multiple different proposed dosing regimens (e.g., varying dose amount, dose interval and/or route of administration) to determine how each dosing regimen would likely impact the patient, as predicted by the patient-specific factors and/or data in the model/composite model.

More specifically, the server 104 performs multiple forecasts of patient responses to evaluate multiple proposed dosing regimens based on the patient's characteristics, by referencing and/or processing the composite model. Then, each dosing regimen is determined to be adequate or inadequate for meeting treatment objective or target profile. For example, the target profile may involve maintenance of a trough blood concentration level above a therapeutic threshold. Further, the server 104 may compare forecasts of patient responses to various dosing regimens, and create a set of satisfactory or best dosing regimens for achieving the treatment objective or target profile. These satisfactory or best dosing regimens may correspond to those dosing regimens that are recommended for the patient 116.

At step 312, the one or more recommended dosing regimens are provided to the user interface 112 in the clinical portal 114. The medical professional 118 may then browse the recommended one or more dosing regimens before selecting a dosing regimen for administration to the patient 116. In doing this, the medical professional 118 may select a dosing regimen from the list, or may modify the recommended dosing regimen, in accordance with his/her judgment. Various considerations may be taken into consideration by the medical professional 118 and/or the server 104 in determining recommended dosing regimens. For example, a primary consideration may be meeting a specific treatment objective, such as maintaining a minimum blood level concentration or maintaining a target blood pressure, for example. However, other considerations may also be taken into consideration, such as ease of compliance, scheduling consideration, or medication/treatment cost, for example. The system may include utility functions for taking such other considerations into account when determining the recommended dosing regimens. Then, the medical professional 118 directly or indirectly administers the dosing regimen (which may be the same or different from the recommended dosing regimen) to the patient, and later follows up with the patient 116 to check the patient's response to the dosing regimen.

In some implementations, the recommended dosing regimen is provided with a confidence interval that indicates a likelihood that the particular dosing regimen will be therapeutically effective for the patient 116. In particular, the confidence interval of the projected response or concentration from the individual data may be assessed based on the complexity of the multiple computational models and the amount of individual data (PK and/or PD data). In particular, the confidence interval may reflect the possible error in the individual predictions from the models. Initially, when no individual measurements have been taken from the patient 116, the model's predictions have an error associated with them that is approximately equal to the unexplained variability in the PK and the PD models. However, as individual measurements are taken and introduced into these models, the error (or equivalently, the confidence interval) decreases before ultimately approaching the assay error, which may correspond to a measurement error. Moreover, the confidence intervals may be provided to the clinical portal 114, to give the medical professional 118 a sense for the amount of error remaining in the model predictions.

At step 314, the patient's response data is received, and at decision block 316, it is determined whether to re-run or update the model. In particular, the medical professional 118 may determine that an adjustment to the dosing regimen is warranted if the patient's response is deficient or not as expected. In this case, the medical professional 118 may take additional measurements from the patient 116, and provide these additional measurements to the clinical portal 114. Alternatively, the medical professional 118 may provide the patient's response data to the server 104, which determines whether the patient's response is as expected or deficient, and subsequently determines whether to re-run the model. If it is determined to not re-run the model, the method 300 ends or returns to step 314 to receive additional patient response data and re-evaluates whether to re-run the model at decision block 316.

If it is determined to re-run the model, the method 300 returns to step 308 to provide the patient response data received at step 314 to the model. In particular, as is described in the '545 application, a Bayesian update process may be used to update the composite model based on the patient's response to the dosing regimen. Each of the underlying mathematical models are updated to reflect the patient's specific characteristics and response. Generally, Bayesian updating involves a Bayesian inference, which is a method in which Bayes' rule is used to update the probability estimate for a hypothesis as additional evidence is obtained. Bayesian updating is especially important in the dynamic analysis of data collected over time (sequentially). The method as applied here uses models that describe not only the time course of exposure and/or response, but also include terms describing the unexplained (random) variability of exposure and response. The result of Bayesian updating is a set of parameters conditional to the observed data. The process involves sampling parameters from a prior distribution (e.g., the underlying models) and calculating the expected responses based on the underlying models. For each underlying model, the difference between the model expectation and the observed data is compared. This difference is referred to as the "objective function." The parameters are then adjusted based on the objective function, and the new parameters are tested against the observed data by comparing the difference between the new model expectation and the observed data. This process runs iteratively until the objective function is minimized, suggesting that the parameters that minimize the objective function best describe the current data. All underlying models are thus subjected to Bayesian updating. Once all models have been updated, Bayesian averaging may be repeated to produce a new composite model. In some implementations, a random function may be used to interject some variation to ensure that a global minimum of the objective function has been obtained.

Figure 4A:
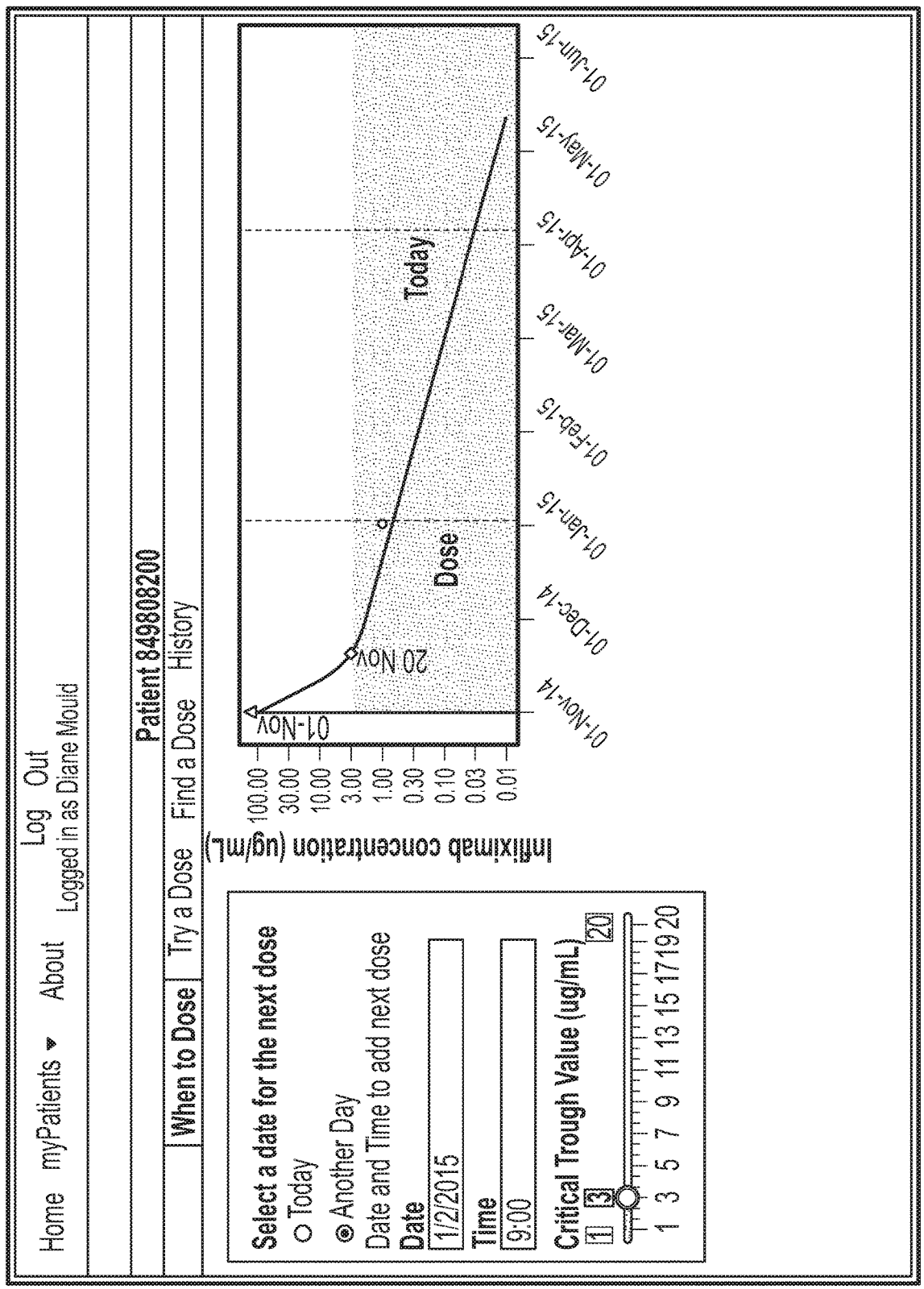
FIGS. 4A and 4B are example displays of a user interface on a clinical portal that provide graphs of predicted concentration time profiles, according to an illustrative implementation.

FIGS. 4A, 4B, 5A, and 5B are example displays of the user interface 112 on the clinical portal 114, according to an illustrative implementation. The display shown in FIG. 4A provides a screen that includes the IFX model predictions in accordance with the model described in relation to EQS. 1-16. In particular, the image on the right side of FIG. 4A depicts a predicted IFX concentration in a solid curve (as assessed by the PK/PD model) on the y-axis versus time on the x-axis. As is shown in FIG. 4A, a critical trough value (in µg/mL) is set by the user (or by default) to a value of 3 µg/mL. The critical trough value corresponds to a threshold concentration level, where it is undesirable for the patient's concentration to be below the critical trough value. The triangle in FIG. 4A indicates a dose of IFX that is administered to the patient (e.g., last administered on Nov. 1, 2014), and the graph indicates that the model predicts that the patient's concentration of IFX will hit the critical trough value on Nov. 20, 2014, and the graph suggests that another administration of a dose of IFX may be administered on that date. The solid dot near Jan. 1, 2015 indicates the measured IFX concentration, and represents the patient's measurement data to which the model predictions are fit.

Figure 4B:
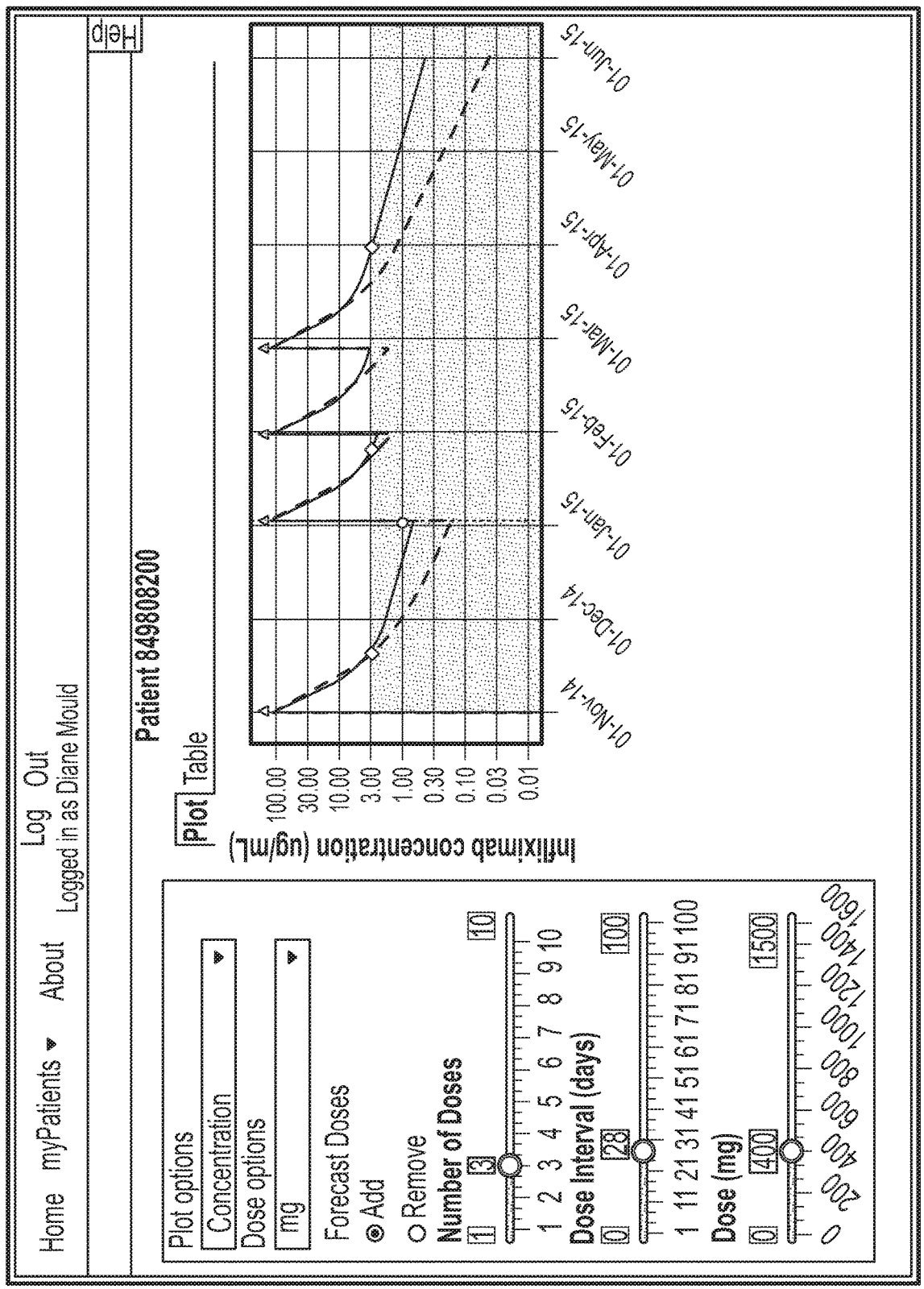

In FIG. 4B, the user has provided an input dosing regimen for testing by the model. In particular, the user has set the number of doses to three, the dose interval to 28 days, and the dose to 400 mg. In this case, the systems and methods of the present disclosure provide a predicted concentration profile for a specific patient based on the input dosing regimen (solid line), where the three doses are administered every 28 days beginning Jan. 1, 2015, and are indicated by the triangles at the top of the graph. The graph also includes markers at locations where the predicted concentration profile (solid line) intersects the critical trough value (of 3 µg/mL). In particular, the feedback from the model in FIG. 4B is that the input dosing regimen provided by the user is insufficient to keep the patient's predicted concentration level entirely above the critical trough value between doses, but is very close to achieving this goal. In this case, the user may adjust the input dosing regimen to lower the dose interval, increase the dose, or a combination thereof. In addition, the graph shown in FIG. 4B includes a dashed line, which is representative of a typical patient's concentration time profile, and is not based on the patient's individual measurements.

Figure 5A:
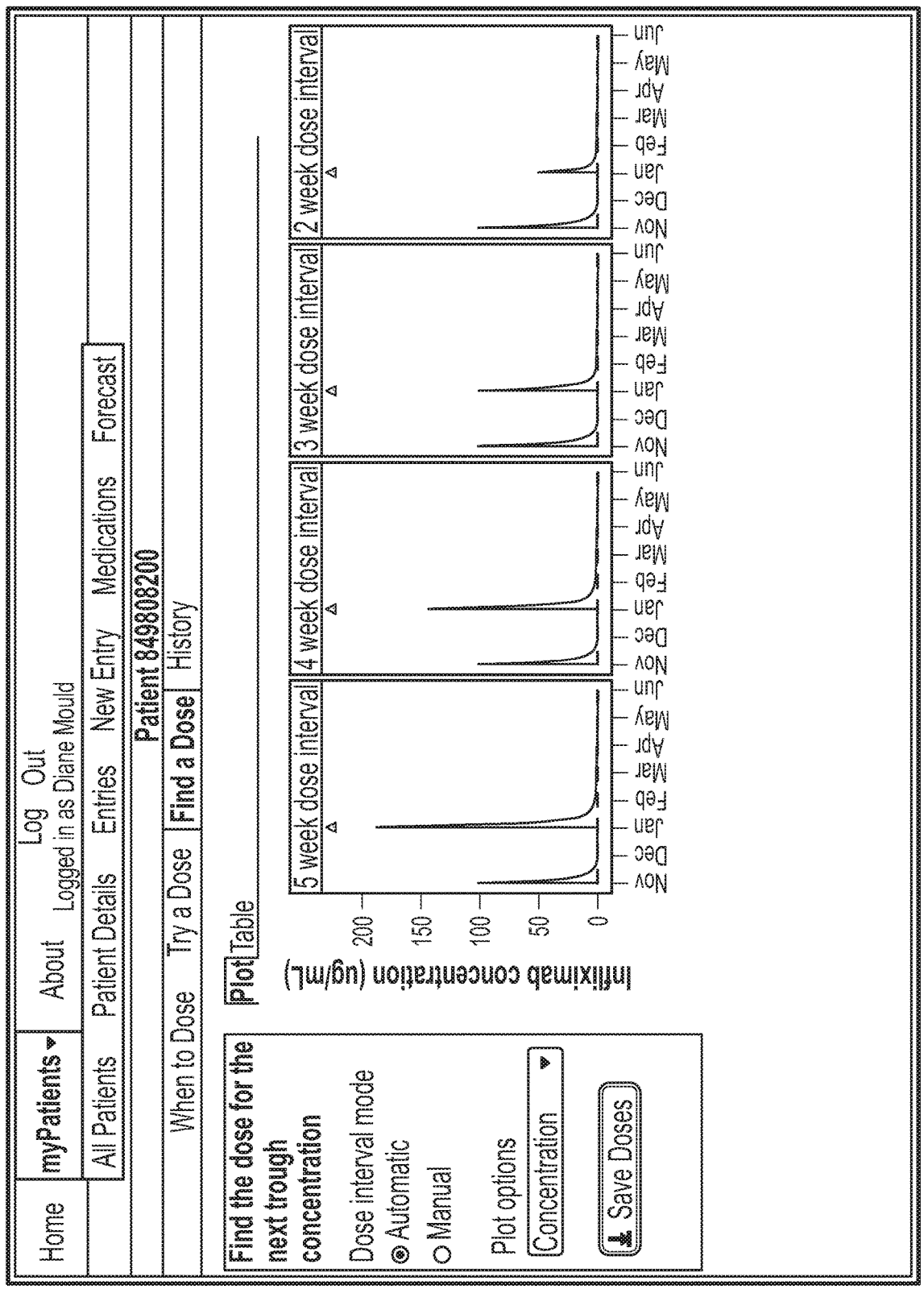

FIG. 5A depicts an example display screen that displays predicted concentration time profiles for four different dosing regimens. In particular, each dosing regimen has a corresponding dose interval (5 weeks, 4 weeks, 3 weeks, and 2 weeks), where the dose amount decreases as dose interval decreases (as is indicated by the height of the second peak in each predicted concentration time profile). In this case, the user has selected to plot IFX concentration versus time, and to allow the computational models to run to identify recommended dosing regimens to maintain IFX concentrations above the critical trough value.

In FIG. 5B, the user has selected to display the results from the plot shown in FIG. 5A in a table form. In particular, the example display screen in FIG. 5B lists the last dose date (Jan. 2, 2015), various dosing intervals, a trough date (corresponding to the first date after the dose date that the predicted concentration time profile falls to or at the critical trough value), the suggested dose (in mg), the normalized suggested dose (in mg/kg), the number of vials used for each dose, and the target concentration (in ng/ml). As is shown in FIG. 5B, a set of proposed dosing schedules is shown, where the dosing schedules have different dose intervals ranging from two to eight weeks. While some of the dosing schedules with longer dose intervals (six to eight weeks) are not recommended, four dosing schedules (with dose intervals of two to five weeks) are proposed with doses that increase as dose interval increases. In particular, when interacting with the display screen of FIG. 5B, the medical professional 118 may select a dosing regimen based on a specific goal. For example, the longer dose interval (e.g., five weeks) may be selected if it is desirable to administer doses to the patient 116 infrequently. Alternatively, since patients are often charged the price of a full vial, even when a partial vial is used, it may be desirable to use as much of the vials as possible. In this case, the four-week dosing regimen may be selected, since 4.9 vials are used for each dose, and leads to little wastage of the drug (e.g., only 0.1 vials per dosage). Alternatively, a shorter dose interval (e.g., two weeks) may be selected it if is desirable to administer doses to the patient 116 more frequently, or to charge the patient 116 for only two vials at a time.

Figure 6:
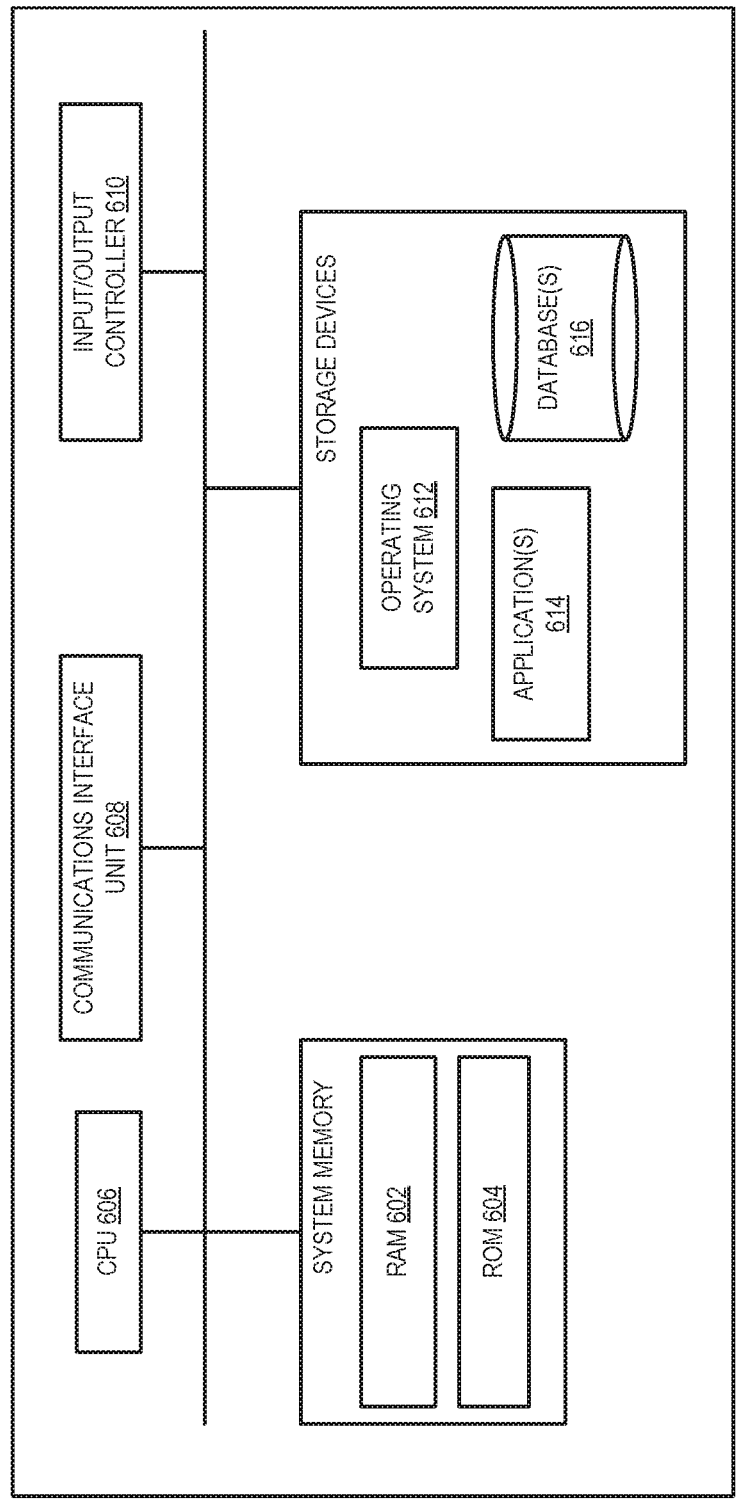
FIG. 6 is a block diagram of a computing device for performing any of the processes described herein, according to an illustrative implementation.

FIG. 6 is a block diagram of a computing device, such as any of the components of the systems of FIGS. 1A-1C, for performing any of the processes described herein. Each of the components of these systems may be implemented on one or more computing devices 600. In certain aspects, a plurality of the components of these systems may be included within one computing device 600. In certain implementations, a component and a storage device may be implemented across several computing devices 600.

The computing device 600 includes at least one communications interface unit, an input/output controller 610, system memory, and one or more data storage devices. The system memory includes at least one random access memory (RAM 602) and at least one read-only memory (ROM 604). All of these elements are in communication with a central processing unit (CPU 606) to facilitate the operation of the computing device 600. The computing device 600 may be configured in many different ways. For example, the computing device 600 may be a conventional standalone computer or alternatively, the functions of computing device 600 may be distributed across multiple computer systems and architectures. In FIG. 6, the computing device 600 is linked, via network or local network, to other servers or systems.

The computing device 600 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 608 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 606 includes a processor, such as one or more conventional microprocessors and one or more supplementary co-processors such as math co-processors for offloading workload from the CPU 606. The CPU 606 is in communication with the communications interface unit 608 and the input/output controller 610, through which the CPU 606 communicates with other devices such as other servers, user terminals, or devices. The communications interface unit 608 and the input/output controller 610 may include multiple communication channels for simultaneous communication with, for example, other processors, servers or client terminals.

The CPU 606 is also in communication with the data storage device. The data storage device may include an appropriate combination of magnetic, optical or semiconductor memory, and may include, for example, RAM 602, ROM 604, flash drive, an optical disc such as a compact disc or a hard disk or drive. The CPU 606 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 606 may be connected to the data storage device via the communications interface unit 608. The CPU 606 may be configured to perform one or more particular processing functions.

The data storage device may store, for example, (i) an operating system 612 for the computing device 600; (ii) one or more applications 614 (e.g., computer program code or a computer program product) adapted to direct the CPU 606 in accordance with the systems and methods described here, and particularly in accordance with the processes described in detail with regard to the CPU 606; or (iii) database(s) 616 adapted to store information that may be utilized to store information required by the program.

The operating system 612 and applications 614 may be stored, for example, in a compressed, an uncompiled and an encrypted format, and may include computer program code. The instructions of the program may be read into a main memory of the processor from a computer-readable medium other than the data storage device, such as from the ROM 604 or from the RAM 602. While execution of sequences of instructions in the program causes the CPU 606 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions described herein. The program also may include program elements such as an operating system 612, a database management system and "device drivers" that allow the processor to interface with computer peripheral devices (e.g., a video display, a keyboard, a computer mouse, etc.) via the input/output controller 610.

The term "computer-readable medium" as used herein refers to any non-transitory medium that provides or participates in providing instructions to the processor of the computing device 600 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 606 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 600 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

It is to be understood that while various illustrative implementations have been described, the forgoing description is merely illustrative and does not limit the scope of the invention. While several examples have been provided in the present disclosure, it should be understood that the disclosed systems, components and methods of manufacture may be embodied in many other specific forms without departing from the scope of the present disclosure.

The examples disclosed can be implemented in combinations or sub-combinations with one or more other features described herein. A variety of apparatus, systems and methods may be implemented based on the disclosure and still fall within the scope of the invention. Also, the various features described or illustrated above may be combined or integrated in other systems or certain features may be omitted, or not implemented.

While various implementations of the present disclosure have been shown and described herein, it will be obvious to those skilled in the art that such implementations are provided by way of example only. Numerous variations, changes, and substitutions will now occur to those skilled in the art without departing from the disclosure. It should be understood that various alternatives to the implementations of the disclosure described herein may be employed in practicing the disclosure.

All references cited herein are incorporated by reference in their entirety and made part of this application.

The invention claimed is:

1. A method for treating an individual with a personalized dose of a pharmaceutical, the method comprising:
receiving, at an input port:
first data representative of one or more characteristics of the individual prior to administration of the pharmaceutical, wherein the characteristics of the individual include at least one of sex, age, weight, race, disease stage, disease status, prior therapy, concomitant diseases, demographic information, and laboratory test result information; and
second data representative of a measurement of a physiological parameter of the individual after administration of the pharmaceutical, wherein the physiological parameter is a measured concentration time profile of the pharmaceutical or a biomarker in the individual's blood, tissue, or cells;
accessing a computer processor in communication with the input port and an electronic database;
receiving, by the computer processor, information that represents a computational model stored in the electronic database, wherein the computational model provides a prediction of an effect of the pharmaceutical on the individual's body, the computational model being a function of response profiles for a population of patients and patient factor covariates corresponding to the characteristics of the individual, the computational model including a pharmacokinetic component including a pharmacokinetic clearance and a pharmacodynamic component including a pharmacodynamic response, the computational model describing an interrelation between the pharmacokinetic component and the pharmacodynamic component wherein the pharmacokinetic clearance is modified to include a diminishing effect of the pharmacodynamic response on the pharmacokinetic clearance over time:
providing, based on the first data and the computational model, a first target concentration and one or more first doses determined by Bayesian analysis to likely achieve the first target concentration for the pharmaceutical in the individual's body;
preparing an updated computational model by performing, using the processor and based on the second data, a Bayesian update to the pharmacokinetic component and the pharmacodynamic component of the computational model; wherein the updated computational model reflects the measurement of the physiological parameter of the individual, wherein the second data indicates a response by the individual to the one or more first doses;
providing, based on the updated computational model, a second target concentration and one or more second doses, likely to achieve the second target concentration for the pharmaceutical in the individual's body, wherein the update to the pharmacodynamic component of the computational model is used to predict that the second target concentration will have a therapeutic effect on the individual;
providing one or more recommended dosing regimens for administration to the individual, the one or more recommended dosing regimens corresponding to the one or more second doses;
selecting, from among the one or more recommended dosing regimens, a personalized dosing regimen of the pharmaceutical; and
administering the pharmaceutical to the individual according to the selected personalized dosing regimen.

2. The method of claim 1, wherein the pharmacokinetic component of the computational model includes a compartmental model, and further comprising using the computer processor to predict a concentration time profile of the pharmaceutical in at least one compartment in the compartmental model based on the pharmacokinetic component.

3. The method of claim 2, further comprising predicting the predicted concentration time profile is by using a first differential equation that describes a flow rate of the pharmaceutical into and out of the at least one compartment in the compartmental model.

4. The method of claim 1, wherein the pharmacodynamic component of the computational model includes a synthesis rate parameter representative of a synthesis rate of a pharmacodynamic marker and a degradation rate parameter representative of a degradation rate of the pharmacodynamic marker, and further comprising predicting the individual's response to the pharmaceutical using a second differential equation that admits the synthesis rate parameter and the degradation rate parameter.

5. The system method of claim 1, wherein Bayesian analysis comprises comparing the measured concentration time profile to the predicted concentration time profile.

6. The method of claim 5, wherein Bayesian analysis further comprises performing an optimization technique to minimize a difference between the measured concentration time profile and the predicted concentration time profile.

7. The method of claim 3, wherein the pharmaceutical is infliximab, and the pharmacodynamic component of the computational model reflects an effect of infliximab on the individual's body.

8. The method of claim 7, wherein the flow rate accounts for the individual's predicted response to the infliximab as the individual heals.

9. The method of claim 1, wherein the first target concentration and the second target concentration each corresponds to a concentration that is predicted to cause an effect in the individual's body that is half of a predicted maximal effect.

10. The method of claim 1, wherein the first data and the second data each include an anonymized identifier for the individual, and the first target concentration and the one or more first doses are portions of a first dosing regimen that includes recommended times and doses to administer to the individual.

11. A method for administering a personalized dose of a pharmaceutical to an individual known to have an indication treatable with the pharmaceutical, the method comprising:
receiving, at an input port, first data representative of one or more characteristics of the individual prior to administration of the pharmaceutical, wherein the characteristics of the individual include at least one of sex, age, weight, race, disease stage, disease status, prior therapy, concomitant diseases, demographic information, and laboratory test result information;
generating, at a computer processor, based on the first data and a computational model, a first target concentration and one or more first doses determined by Bayesian analysis to likely achieve the first target concentration for the pharmaceutical in the individual's body, wherein the computer processor is in communication with the input port and an electronic database having information that represents the computational model to predict an effect of the pharmaceutical on the individual's body, the computational model being a function of response profiles for a population of patients and patient factor covariates corresponding to the characteristics of the individual, the computational model including a pharmacokinetic component including a pharmacokinetic clearance and a pharmacodynamic component including a pharmacodynamic response, the computational model describing an interrelation between the pharmacokinetic component and the pharmacodynamic component wherein the pharmacokinetic clearance is modified to include a diminishing effect of the pharmacodynamic response on the pharmacokinetic clearance over time;
receiving, at the input port, second data representative of a measurement of a physiological parameter of the individual after administration of the pharmaceutical, wherein the physiological parameter is a measured concentration time profile of the pharmaceutical or a biomarker in the individual's blood, tissue, or cells, wherein the second data indicates a response by the individual to the one or more first doses;
computing, based on the second data, a Bayesian update to the pharmacokinetic component and the pharmacodynamic component of the computational model to obtain an updated computational model that reflects the measurement of the physiological parameter of the individual;
generating, based on the updated computational model, a second target concentration and one or more second doses determined by Bayesian analysis to likely achieve the second target concentration for the pharmaceutical in the individual's body, wherein the update to the pharmacodynamic component of the computational model is used to predict that the second target concentration will have a therapeutic effect on the individual; and
administering one or more recommended dosing regimens to the individual, the one or more recommended dosing regimens corresponding to the one or more second doses.

12. The method of claim 11, wherein the pharmacokinetic component of the computational model includes a compartmental model, and the method further comprises using the pharmacokinetic component to predict a concentration time profile of the pharmaceutical in at least one compartment in the compartmental model.

13. The method of claim 12, further comprising predicting the predicted concentration time profile by using a first differential equation that describes a flow rate of the pharmaceutical into and out of the at least one compartment in the compartmental model.

14. The method of claim 11, wherein the pharmacodynamic component of the computational model includes a synthesis rate parameter representative of a synthesis rate of a pharmacodynamic marker and a degradation rate parameter representative of a degradation rate of the pharmacodynamic marker, and further comprising using the synthesis rate parameter and the degradation rate parameter arc used in a second differential equation that predicts the individual's response to the pharmaceutical.

15. The method of claim 11, wherein the Bayesian analysis comprises comparing the measured concentration time profile to the predicted concentration time profile.

16. The method of claim 12, wherein the Bayesian analysis further comprises performing an optimization technique to minimize a difference between the measured concentration time profile and the predicted concentration.

17. The method of claim 13, wherein the pharmaceutical is infliximab, and the pharmacodynamic component of the computational model reflects an effect of infliximab on the individual's body.

18. The method of claim 17, wherein the flow rate accounts for the individual's predicted response to the infliximab as the individual heals.

19. The method of claim 11, wherein the first target concentration and the second target concentration each corresponds to a concentration that is predicted to cause an effect in the individual's body that is half of a predicted maximal effect.

20. The method of claim 11, wherein the first data and the second data each include an anonymized identifier for the individual, and the first target concentration and the one or more first doses are portions of a first dosing regimen that includes recommended times and doses to administer to the individual.

\* \* \* \* \*

UNITED STATES PATENT AND TRADEMARK OFFICE
CERTIFICATE OF CORRECTION

| | | |
|---|---|---|
| PATENT NO. | : 11,501,863 B2 | |
| APPLICATION NO. | : 15/094379 | |
| DATED | : November 15, 2022 | |
| INVENTOR(S) | : Diane R. Mould | |

It is certified that error appears in the above-identified patent and that said Letters Patent is hereby corrected as shown below:

In the Claims

Column 28, Line 63, should read as follows:
3. The method of claim 2, further comprising predicting the predicted concentration time profile by using a first differential equation that describes a flow rate of the pharmaceutical into and out of the at least one compartment in the compartmental model.

Column 29, Line 10, should read as follows:
5. The method of claim 1, wherein Bayesian analysis comprises comparing the measured concentration time profile to the predicted concentration time profile.

Column 30, Line 40, should read as follows:
14. The method of claim 11, wherein the pharmacodynamic component of the computational model includes a synthesis rate parameter representative of a synthesis rate of a pharmacodynamic marker and a degradation rate parameter representative of a degradation rate of the pharmacodynamic marker, and further comprising using the synthesis rate parameter and the degradation rate parameter in a second differential equation that predicts the individual's response to the pharmaceutical.

Signed and Sealed this
Twenty-eighth Day of March, 2023

Katherine Kelly Vidal
*Director of the United States Patent and Trademark Office*